(12) United States Patent
Matschiner et al.

(10) Patent No.: US 9,260,492 B2
(45) Date of Patent: Feb. 16, 2016

(54) MUTEINS OF HUMAN LIPOCALIN 2 WITH AFFINITY FOR GLYPICAN-3 (GPC-3)

(75) Inventors: Gabriele Matschiner, Munich (DE); Andreas Hohlbaum, Paunzhausen (DE); Kristian Jensen, Landshut (DE)

(73) Assignee: Pieris AG, Freising-Weihenstephan (DE)

(*) Notice: Subject to any disclaimer, the term of this patent is extended or adjusted under 35 U.S.C. 154(b) by 244 days.

(21) Appl. No.: 13/885,229

(22) PCT Filed: Nov. 15, 2011

(86) PCT No.: PCT/EP2011/070119
§ 371 (c)(1),
(2), (4) Date: Jul. 26, 2013

(87) PCT Pub. No.: WO2012/065978
PCT Pub. Date: May 24, 2012

(65) Prior Publication Data
US 2013/0296258 A1 Nov. 7, 2013

Related U.S. Application Data

(60) Provisional application No. 61/413,706, filed on Nov. 15, 2010.

(30) Foreign Application Priority Data

Nov. 15, 2010 (EP) .................................... 10191228

(51) Int. Cl.
| | |
|---|---|
| C07K 14/435 | (2006.01) |
| C12N 9/96 | (2006.01) |
| C07K 16/44 | (2006.01) |
| A61K 38/00 | (2006.01) |
| C07K 14/47 | (2006.01) |
| C07K 16/00 | (2006.01) |
| C12P 21/08 | (2006.01) |

(52) U.S. Cl.
CPC ............... *C07K 14/435* (2013.01); *A61K 38/00* (2013.01); *C07K 14/47* (2013.01); *C07K 14/4725* (2013.01); *C07K 16/44* (2013.01); *C12N 9/96* (2013.01)

(58) Field of Classification Search
None
See application file for complete search history.

(56) References Cited

U.S. PATENT DOCUMENTS

| | | | |
|---|---|---|---|
| 5,728,553 A | 3/1998 | Goodey et al. | |
| 6,177,074 B1 | 1/2001 | Glue et al. | |
| 6,403,564 B1 | 6/2002 | Ganguly et al. | |
| 6,500,930 B2 | 12/2002 | Adamson | |
| 6,620,413 B1 | 9/2003 | DeSauvage et al. | |
| 6,696,245 B2 | 2/2004 | Winter et al. | |
| 7,235,520 B2 * | 6/2007 | Green et al. | 514/18.9 |
| 7,250,297 B1 | 7/2007 | Beste et al. | |
| 2003/0069395 A1 | 4/2003 | Sato et al. | |

FOREIGN PATENT DOCUMENTS

| | | |
|---|---|---|
| EP | 0 330 451 A2 | 8/1989 |
| EP | 0 361 991 A2 | 4/1990 |
| WO | WO 99/16873 A1 | 4/1999 |
| WO | WO 99/64016 A1 | 12/1999 |
| WO | WO 00/75308 A1 | 12/2000 |
| WO | WO 03/029462 A1 | 4/2003 |
| WO | WO 03/029463 A2 | 4/2003 |
| WO | WO 03/029471 A1 | 4/2003 |
| WO | WO 2005/019254 A1 | 3/2005 |
| WO | WO 2005/019255 A1 | 3/2005 |
| WO | WO 2005/019256 A | 3/2005 |
| WO | WO 2006/056464 A2 | 6/2006 |
| WO | WO 2007/038619 A2 | 4/2007 |
| WO | WO 2007/047291 A2 | 4/2007 |
| WO | WO 2007/137170 A2 | 11/2007 |
| WO | WO 2009/012394 A1 | 1/2009 |
| WO | WO2009/156456 * | 12/2009 |
| WO | WO 2012/065978 A1 | 5/2012 |

OTHER PUBLICATIONS

Wells, Biochemistry, 1990 vol. 29, pp. 8509-8517.*
Bork, Genome Research, 2000, vol. 10, pp. 398-400.*
Skolnick et al., Trends in Biotech, 2000, vol. 18, No. 1, pp. 34-39.*
Doerks et al., Trends in Genetics, 1998, vol. 14, pp. 248-250.*
Tokuriki and Tawflik, (Current Opinion in Structural Biology, 2009, vol. 19, pp. 596-604.*
Wang et al. (Nuc. Acids Res. 27: 4609-4618, 1999; p. 4617.*
Kaufman et al (Blood 94: 3178-3184, 1999.*
Bundgaard; UNIPROT:P80188; 1994.*
Altschul, et al., "Gapped BLAST and PSI-BLAST a new generation of protein database search programs," *Nucleic Acids Research*, Jul. 16, 1997, 25:3389-3402.
Altuvia et al., "Ranking potential binding peptides to MHC molecules by a computational threading approach," *J. Mol. Biol.*, 1995, 249:244-250.
Amstutz, P. et al., "In vitro display technologies novel developments and applications," *Current Opinion in Biotechnology*, 2001, 12:400-405.
Bachmann, "Linkage map of *Escherichia coli* K-12, edition 8," *Microbiological Reviews*, Jun. 1990, 54(2):130-197.

(Continued)

*Primary Examiner* — Bridget E Bunner
*Assistant Examiner* — Fozia Hamud
(74) *Attorney, Agent, or Firm* — Foley & Lardner LLP

(57) ABSTRACT

Described are specific-binding therapeutic and/or diagnostic proteins directed against Glypican-3 (GPC3), which proteins include muteins of a lipocalin protein, such as lipocalin 2 (Lcn2 or NGAL). The invention also relates to nucleic acid molecules encoding such proteins and to methods for generation and use of such proteins and nucleic acid molecules. Accordingly, the invention also is directed to pharmaceutical and/or diagnostic compositions comprising such lipocalin proteins, including uses of these proteins.

18 Claims, 9 Drawing Sheets

(56) References Cited

OTHER PUBLICATIONS

Beste et al., "Small antibody-like proteins with prescribed ligand specificities derived from the lipocalin fold," *PNAS*, Mar. 1999, 96:1898-1903.
Binder et al., "High-throughput sorting of an anticalin library via EspP-mediated functional display on the *Escherichia coli* cell surface," *Journal of Molecular Biology*, Jul. 23, 2010, 400(4):783-802.
Bittker, J. A. et al., "Nucleic acid evolution and minimization by nonhomologous random recombination," *Nature Biotechnology*, Oct. 2002, 20:1024-1029.
Breustedt et al., "Comparative ligand-binding analysis of ten human lipocalins," *Biochimica et Biophysica Acta*, 2006, 1764:161-173.
Bruckdorfer, T. et al., "From production of peptides in milligram amounts for research to multi-tons quantities for drugs of the future," (2004) *Current Pharmaceutical Biotechnology*, 2004, 5:29-43.
Bullock et al., "XL1-Blue: A high efficiency plasmid transforming a recA *Escherichia coli* strain with beta-galactosidase selection," *BioTechniques*, 1987, 5(4):376-378.
Dennis, M. S. et al., "Albumin binding as a general strategy for improving the pharmacokinetics of proteins," *The Journal of Biological Chemistry*, Sep. 20, 2002, 277(38):35035-35043.
Fling et al., "Peptide and protein molecular weight determination by electrophoresis using a high-molarity tris buffer system without urea," *Analytical Biochemistry*, 1986, 155:83-88.
Flower et al., "The lipocalin protein family: structural and sequence overview," *Biochimica et Biophysica Acta*, 2000, 1482:9-24.
Fuertges et al., "The clinical efficacy of poly(ethylene glycol)-modified proteins," *Journal of Controlled Release*, 1990, 11:139-148.
Gaillard et al., "Diphtheria toxin receptor-targeted brain drug delivery," *International Congress Series*, 2005, 1277:185-198.
Gaillard et al., "Targeted delivery across the blood-brain barrier," *Expert Opin. Drug Deliv.*, 2005, 2(2):299-309.
Gebauer et al., "Engineered protein scaffolds as next-generation antibody therapeutics," *Current Opinion in Chemical Biology*, Jun. 1, 2009, 13:245-255.
Goetz et al., "Ligand preference inferred from the structure of neutrophil gelatinase associated lipocalin," *Biochemistry*, 2000, 39:1935-1941.
Holhbaum, et al., "Anticalins (R): The lipocalin family as a novel protein scaffold for the development of next-generation immunotherapies," *Expert Review of Clinical Immunology*, Jan. 1, 2007, 3(4):491-501.
Holliger et al., "Diabodies small bivalent and bispecific antibody fragments," *PNAS*, Jul. 1993, 90:6444-6448.
Ill et al., "Design and construction of a hybrid immunoglobulin domain with properties of both heavy and light chain variable regions," *Protein Engineering*, 1997, 10(8):949-957.
International Search Report and Written Opinion of the International Searching Authority issued in International Application No. PCT/EP2011/070119 dated Jun. 3, 2012.
Jakubovic et al., "Glypican-3: From the mutations of Simpson-Golabi-Behmel genetic syndrome to a tumor marker for hepatocellular carcinoma," *Experimental and Molecular Pathology*, 2007, 82:184-189.
Kay et al., "High-throughput screening strategies to identify inhibitors of protein-protein interactions," *Molecular Diversity*, 1995, 1:139-140.
Kim et al., "High-affinity recognition of lanthanide(III) chelate complexes by a reprogrammed human lipocalin 2," *J. Am. Chem. Soc.*, 2009, 131(10):3565-3576.
König et al., "Use of an albumin-binding domain for the selective immobilisation of recombinant capture antibody fragments on ELISA plates," *Journal of Immunological Methods*, Jun. 8, 1998, 218:73-83.
Martin et al., "The affinity-selection of a minibody polypeptide inhibitor of human interleukin-6," *The EMBO Journal*, 1994, 13(22):5303-5309.
Mateo et al., "Removal of amphipathic epitopes from genetically engineered antibodies: Production of modified immunoglobulins with reduced immunogenicity," *Hybridoma*, Aug. 30, 2000, 19(6):463-471.
Meidan et al "Emerging technologies in transdermal therapeutics," *American Journal of Therapeutics*, 2004, 11(4):312-316.
Murakami, H et al., "Random insertion and deletion of arbitrary number of bases for codon-based random mutation of DNAs," *Nature Biotechnology*, Jan. 2002, 20:76-81.
Nakatsura et al., "Usefulness of the novel oncofetal antigen glypican-3 for diagnosis of heptocellular carcinoma and melanoma," *BioDrugs*, 2005, 19(2):71-77.
Osborn, B.L. et al., "Pharmacokinetic and pharmacodynamic studies of a human serum albumin-interferon-3B1 fusion protein in cynomolgus monkeys" *The Journal of Pharmacology and Experimental Therapeutics*, Jul. 12, 2002, 303(2):540-548.
Parikh et al., "Hepatocellular cancer: A guide for the internist," *The American Journal of Medicine*, 2007, 120:194-202.
Pini et al., "Phage Display and Colony Filter Screening for High-Throughput Selection of Antibody Libraries," *Combinatorial Chemistry High Throughput Screening*, 2002, 5:503-510.
Sasisekharan et al., "Roles of heparan-sulphate glycosaminoglycans in cancer," *Nature Reviews Cancer*, Jul. 2002, 2:521-528.
Schiweck et al., "Fermenter production of an artificial fab fragment rationally designed for the antigen cystatin and its optimized crystallization through constant domain shuffling," *Proteins: Structure, Function, and Genetics*, 1995, 23:561-565.
Schlehuber et al., "A novel type of receptor protein, based on the lipocalin scaffold, with specificity for digoxigenin," *J. Mol. Biol.*, 2000, 297:1105-1120.
Schlehuber et al., "Duocalins, engineered ligand-binding proteins with dual specificity derived from the lipocalin fold," *Biol. Chem.*, Sep. 2001, 382:1335-1342.
Schmidt et al., "Molecular interaction between the strep-tag affinity peptide and its cognate target, streptavidin," *J. Mol. Biol.*, 1996, 255:753-766.
Silverman et al., "Multivalent avimer proteins evolved by exon shuffling of a family of human receptor domains," *Nature Biotechnology*, Dec. 2005, 23(12):1556-1561.
Skerra et al., "Use of the Strep-tag and streptavidin for detection and purification of recombinant proteins," *Methods in Enzymology*, 2000, 326:271-304.
Skerra, "Anticalins as alternative binding proteins for therapeutic use," *Current Opinion in Molecular Therapeutics*, Aug. 1, 2007, 9(4):336-344.
Skerra, "Anticalins': a new class of engineered ligand-binding proteins with antibody-like properties," *Reviews in Molecular Biotechnology*, 2001, 74:257-275.
Traunecker et al., "Bispecific single chain molecules (Janusins) target cytotoxic lymphocytes on HIV infected cells," *The EMBO Journal*, 1991, 10(12):3655-3659.
Traunecker et al., "Janusin: New molecular design for bispecific reagents," *International Journal of Cancer*, 1992, 7:51-52.
Vajo et al., "Genetically engineered insulin analogs: diabetes in the new millennium," *Pharmacological Reviews*, 2000, 52(1):1-9.
Venturi et al., "High level production of functional antibody fab fragments in an oxidizing bacterial cytoplasm," *J. Mol. Biol.*, 2002, 315:1-8.
Vogt et al., "Bacterially produced apolipoprotein D binds progesterone and arachidonic acid, but not bilirubin or E-3M2H," *Journal of Molecular Recognition*, 2001, 14:79-86.
Wilson et al., "The use of mRNA display to select high-affinity protein-binding peptides," *PNAS*, Mar. 27, 2001, 98(7):3750-3755.
Yanisch-Perron et al., "Improved M13 phage cloning vectors and host strains: nucleotide sequences of the M13mp18 and pUC19 vectors," *Gene*, 1985, 33:103-119.
Zaccolo et al., "An approach to random mutagenesis of DNA using mixtures of triphosphate derivatives of nucleoside analogues," *J. Mol. Biol.*, 1996, 255:589-603.

* cited by examiner

FIGURE 1

```
  1 CCAATTCCATGGGAAATGGTATGTCTCGTGGGnnnGCCGGAAATnnnnnnCTGCGTGAGGATAAGGATCCGnnnAAAATGnnnGCCGACCAT   90
    +---------+---------+---------+---------+---------+---------+---------+---------+---------+
    GGTTAAGGTACCCTTTACCATACAGAGCACCCGGACCCGGCCTTTACGGTAAGACGCACTCCTATTCCTAGGCGTCTTTTACATACGCTGGTA
    GlnPheHisGlyLysTrpTyrValValGlyXaaAlaGlyAsnXaaXaaLeuArgGluAspLysMetXaaAlaThrIle
                            8                     12 13                    21   24

91 TTACGAGTTGAAAGAAGATAAATCATATAACGTCACCnnnGTGnnnTTTnnnnnnAAGAAATGCnnnTACnnnATTnnnACCTTTGTGCC    180
    +---------+---------+---------+---------+---------+---------+---------+---------+---------+
    AATGCTCAACTTTCTTCTATTTAGTATATTGCAGTGGAGGCACACAAAGCGTTTTCTTTACGCTGATGACCTAAGCATGGAAACACGG
    TyrGluLeuLysGluAspLysSerTyrAsnValThrXaaValXaaPheXaaXaaLysLysCysXaaXaaTyrXaaIleXaaThrPheValPro
                                40   42           44 45                 49    51   53

181 GGGGAGCCAGCCGGGCGAGTTTACTTTAGGCnnnATTAAAAGTnnnCCGGGCnnnACATCAnnnTTGGTCCGTCGTGAGCACCAACTA     270
    +---------+---------+---------+---------+---------+---------+---------+---------+---------+
    CCCCTCGGTCGGCCCGCTCAAATGAAATCCGTTGTAATTTCAATGGGCCCGACTGTAGTATGAACCAGGCCAGCACTCGTGGTTGAT
    GlySerGlnProGlyGluPheThrLeuGlyXaaIleLysSerXaaProGlyXaaThrSerXaaValValArgValValSerThrAsnTyr
                                    68                72          75            78

271 CAACCAGCCATGGTGTTCTTCAAGnnnGTGnnnCAGAACCGGCGAGnnnTTTnnnATCACACTGTACGGGCCACGAAAGAACTGAC      360
    +---------+---------+---------+---------+---------+---------+---------+---------+---------+
    GTTGGTCGTACGGTACCACAAGAAGTTCTTTCACAGGGTCTTGGCCGCTCATGAAATTCCATGAAATTTAGTGTGACATGCCCGGTGCTTCTTGACTG
    AsnGlnHisAlaMetValPheLysXaaValXaaGlnAsnArgGluXaaPheXaaIleThrLeuTyrGlyArgThrLysGluLeuThr
                                                    97   99              104 106

361 AAGCGAGCTGAAGGAAAAATTTATCCGCTTTTCCAAATCTCTGG     404      (SEQ ID NO:41)
    +---------+---------+---------+---------+---
    TTCGCTCGACTTCCTTTTAAAATAGGCGAAAAGGTTTAGAGACC            (SEQ ID NO:43)
    SerGluLeuLysGluAsnPheIleArgPheSerLysSerLeu             (SEQ ID NO:42)
```

| Mutein | IC50 [nM] |
|---|---|
| PIE-G3A | 0.6 |
| PIE-G3B | 0.2 |
| PIE-G3C | 1.0 |
| PIE-G3D | 0.7 |
| PIE-G3E | 0.1 |
| PIE-G3F | 0.07 |
| PIE-G3G | 0.1 |
| PIE-G3H | 0.23 |

FIGURE 5

| Mutein | evaluated conc [nM] | $k_{on}$ [$M^{-1}*s^{-1}$] | $k_{off}$ [$s^{-1}$] | KD [nM] |
|---|---|---|---|---|
| PRS-G3A | 40/120 | 1,60E+05 | 6,03E-04 | 3,78 |
| PRS-G3B | 40/120 | 4,38E+05 | 2,42E-04 | 0,55 |
| PRS-G3C | 40/120 | 1,97E+06 | 2,38E-03 | 1,21 |
| PRS-G3D | 40/120 | 7,81E+05 | 1,09E-03 | 1,40 |
| PRS-G3E | 40/120 | 5,11E+06 | 1,78E-03 | 0,35 |
| PRS-G3F | 40/120 | 4,09E+05 | 1,28E-03 | 3,13 |
| PRS-G3G | 40/120 | 1,42E+06 | 7,23E-04 | 0,51 |
| PRS-G3H | 120 | 1,95E+05 | 2,09E-04 | 1,07 |

FIGURE 6

| Mutein | human GPC3-SK-HEP1 EC50 [nM] | cyno GPC3-SK-HEP1 EC50 [nM] | mouse GPC3-SK-HEP1 EC50 [nM] |
|---|---|---|---|
| PIE-G3A | >100 | >100 | n.d. |
| PIE-G3B | 2,5 | 1,1 | 2,9 |
| PIE-G3H | 49 | 98 | 580 |
| PIE-G3E | 0,4 | 0,12 | 2,7 |
| PIE-G3C | 0,5 | 0,2 | 3,5 |
| PIE-G3D | 1 | 0,7 | 10,5 |
| PIE-G3F | 4,7 | 3,2 | 18,7 |
| PIE-G3G | 0,7 | 0,2 | 4,3 |

FIGURE 7

SEQ ID NO: 27

```
Gln Asp Ser Thr Ser Asp Leu Ile Pro Ala Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
            50                  55                  60

Asn Val Thr Ser Val Leu Phe Arg Lys Lys Lys Cys Asp Tyr Trp Ile
 65                 70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
 130                135                 140

Thr Ser Glu Leu Lys Glu Lys Phe Ile Arg Phe Ser Lys Ser Leu Gly
 145                150                 155                 160

Leu Pro Glu Asn His Ile Val Phe Pro Val Pro Ile Asp Gln Cys Ile
                165                 170                 175

Asp Gly
    178
```

FIGURE 8

MUTEINS OF HUMAN LIPOCALIN 2 WITH AFFINITY FOR GLYPICAN-3 (GPC-3)

CROSS REFERENCE TO RELATED APPLICATIONS

This application is the U.S. National Phase of PCT/EP2011/070119, filed Nov. 11, 2011, which was published in English on May 24, 2012 as WO 21012/065978, and claims benefit of the filing date of U.S. Provisional Application No. 61/413,706 and European Application EP 10191228.5, both filed Nov. 15, 2010.

SEQUENCE LISTING

The instant application contains a Sequence Listing which has been submitted in ASCII format via EFS-WEB and is hereby incorporated by reference in its entirety. Said ASCII copy, created on Aug. 7, 2015, is named 029029-0147 SL.txt and is 73,371 bytes in size.

FIELD OF THE INVENTION

The present invention relates to novel, specific-binding therapeutic and/or diagnostic proteins directed against Glypican-3 (GPC3), which proteins preferably are muteins of a lipocalin protein, more preferably of lipocalin 2 (Lcn2 or NGAL). The invention also relates to nucleic acid molecules encoding such proteins and to methods for generation and use of such proteins and nucleic acid molecules. Accordingly, the invention also is directed to pharmaceutical and/or diagnostic compositions comprising such lipocalin proteins, including uses of these proteins.

BACKGROUND

Glypican-3 (GPC3) is an oncofetal antigen that belongs to the glypican family of glycosyl-phosphatidylinositol-anchored heparin sulfate proteoglycans. Glypicans are characterized by a covalent linkage to complex polysaccharide chains called heparinsulphate glycosaminoglycans. Glypicans are involved in cell signaling at the cellular-extracellular matrix interface. (Sasisekharan et al., Nature Reviews I Cancer, Volume 2 (2002).) To date, six distinct members of the human glypican family have been identified. Cell membrane-bound Glypican-3 is composed of two subunits, linked by one or more disulfide bonds.

Glypican-3 is expressed in fetal liver and placenta during development and is down-regulated or silenced in normal adult tissues. Mutations and depletions in the Glypican-3 gene are responsible for the Simpson-Golabi-Behmel or Simpson dysmorphia syndrome in humans. Glypican-3 is expressed in various cancers and, in particular, hepatocellular carcinoma ("HCC"), melanoma, Wilm's tumor, and hepatoblastoma. (Jakubovic and Jothy; Ex. Mol. Path. 82:184-189 (2007); Nakatsura and Nishimura, Biodrugs 19(2):71-77 (2005).)

HCC is the third leading cause of cancer-related deaths worldwide. Each year, HCC accounts for about 1 million deaths. (Nakatsura and Nishimura, Biodrugs 19(2):71-77 (2005)). Hepatitis B virus, hepatitis C virus, and chronic heavy alcohol use leading to cirrhosis of the liver remain the most common causes of HCC. Its incidence has increased dramatically in the United States because of the spread of hepatitis C virus infection and is expected to increase for the next two decades. HCC is treated primarily by liver transplantation or tumor resection. Patient prognosis is dependent on both the underlying liver function and the stage at which the tumor is diagnosed. (Parikh and Hyman, Am J. Med. 120(3): 194-202 (2007).) Effective HCC treatment strategies are needed. It would thus be desirable to have available means and methods for targeting GPC3, preferably GPC3 expressed on tumor cells.

Methods of isolating and analyzing GPC3 as well as agents for the treatment of diseases and conditions associated with GPC3 have been described in WO 2009/012394, WO 2007/137170 or WO 2007/047291. However, no Glypican-3-binding protein having the features attendant to the proteins provided by present invention has been previously described.

SUMMARY OF THE INVENTION

One embodiment of the current invention relates to a lipocalin mutein that is capable of binding Glypican-3 (GPC3) with an affinity measured by a KD of about 10 nM or lower. More preferably, the lipocalins can have an affinity measured by a KD of about 1 nM or 0.3 nM or lower. In another embodiment, the lipocalin mutein is capable of competing for binding to GPC3 in a competition assay preferably with an $IC_{50}$ value of about 1 nM, 0.6 nM or 0.2 nM or lower.

In another embodiment, the invention relates to a lipocalin mutein, wherein said mutein comprises at one or more positions corresponding to position 36, 40, 41, 49, 52, 68, 70, 72, 73, 77, 79, 81, 96, 100, 103, 106, 125, 127, 132, and/or 134 of the linear polypeptide sequence of hLcn2 (SEQ ID NO:27) a substitution, preferably a substitution as described herein.

In particular embodiments, the mutein of the invention comprises at least 1, 2, 3, 4, 5, 6, 7, 8, 9, 10, 11, 12, 13, 14, 15, 16, 17, 18, 19 or 20, sometimes even more, substitutions at a sequence position corresponding to sequence position 36, 40, 41, 49, 52, 68, 70, 72, 73, 77, 79, 81, 96, 100, 103, 106, 125, 127, 132, and/or 134 of the linear polypeptide sequence of NGAL (SEQ ID NO: 27).

Similarly, the invention relates to a polypeptide comprising NGAL shown in SEQ ID NO:27, wherein said NGAL comprises 1, 2, 3, 4, 5, 6, 7, 8, 9, 10, 11, 12, 13, 14, 15, 16, 17, 18, 19 or 20, mutated amino acid residues at the sequence positions 36, 40, 41, 49, 52, 68, 70, 72, 73, 77, 79, 81, 96, 100, 103, 106, 125, 127, 132, and/or 134. Said polypeptide is preferably an anticalin.

In further particular embodiments, a lipocalin mutein according to the current invention comprises an amino acid sequence selected from the group consisting of SEQ ID NOS: 1-8. In another embodiment, the mutein has at least 70% identity to the sequence of a wild-type human lipocalin, including human Lipocalin 2 (hNGAL). Preferably, said mutein comprises 1, 2, 3, 4, 5, 6, 7, 8, 9, 10, 11, 12, 13, 14, 15, 16, 17, 18, 19 or 20, sometimes even more, mutated amino acid residues at the sequence positions 36, 40, 41, 49, 52, 68, 70, 72, 73, 77, 79, 81, 96, 100, 103, 106, 125, 127, 132, and/or 134 of the linear polypeptide sequence of NGAL (SEQ ID NO: 27).

In another embodiment, the mutein of the current invention is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxins, a metal complex, a metal, and colloidal gold. The mutein can be fused at its N-terminus and/or its C-terminus to a fusion partner which is a protein, a protein domain, or a peptide.

In another embodiment, the mutein is conjugated to a compound that extends the serum half-life of the mutein. More preferably, the mutein is conjugated to a compound selected from the group consisting of a polyalkylene glycol molecule, a hydroethylstarch, an Fc part of an immunoglubolin, a CH3 domain of an immoglobulin, a CH4 domain of an immunoglubolin, an albumin binding peptide, and an albumin binding protein.

In another embodiment, the mutein of the current invention is an antagonist of a GPC3.

In another embodiment, the current invention relates to a nucleic acid molecule comprising a nucleotide sequence encoding a mutein of the current invention.

In yet another embodiment, the invention encompasses a host cell containing said nucleic acid molecule.

In another embodiment, the lipocalin mutein of the current invention is selected from the group consisting of muteins of retinol-binding protein (RBP), bilin-binding protein (BBP), apolipoprotein D (APO D), neutrophil gelatinase associated lipocalin (NGAL), tear lipocalin (TLPC), α2-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (hNGAL), human tear lipocalin (hTLPC), human apolipoprotein D (APO D) and the bilin-binding protein of *Pieris brassicae*.

The invention also includes a method of treating a tumor, preferably liver tumor or melanoma, the method comprising administering a pharmaceutical composition containing a mutein as described herein to a subject in need thereof.

DESCRIPTION OF FIGURES

FIG. 1 illustrates the PCR assembly strategy for the simultaneous random mutagenesis of the 20 amino acid positions 36, 40, 41, 49, 52, 68, 70, 72, 73, 77, 79 81, 96, 100, 103, 106, 125, 127, 132, and 134 (underlined and numbered) in the amino acid sequence of the mature Lcn 2. These 20 positions were divided into four sequence subsets. For randomization of the amino acids in each subset an oligodeoxynucleotide was synthesized (SEQ ID NO: 16, SEQ ID NO: 17, SEQ ID NO: 18, SEQ ID NO: 19) wherein NNK mixtures of the nucleotides were employed at the mutated codons. N means a mixture of all four bases A, C, G, and T while K means a mixture of only the two bases G and T; hence such a triplet encodes all 20 natural amino acids as well as the amber stop codon TAG, which is translated as glutamine in the *E. coli* supE-strains XL1-blue (Bullock et al., BioTechniques 5 (1987), 376-378) or TG1 (Sambrook et al., Molecular Cloning. A Laboratory Manual (1989), Cold Spring Harbor Press) that were used for phagemid production and gene expression. Four additional oligodeoxynucleotides (SEQ ID NO: 20, SEQ ID NO: 21, SEQ ID NO: 22, SEQ ID NO: 23) with fixed nucleotide sequences corresponding to the non-coding strand (written below the DNA double strand sequence in 3'-5' direction) and filling the gaps between the aforementioned oligodeoxynucleotides were also used in the assembly reaction. Two shorter flanking oligodeoxynucleotides (SEQ ID NO: 24 and SEQ ID NO: 25), which were added in excess and carried biotin groups, served as primers for the PCR amplification of the assembled, entirely synthetic gene fragment. The two flanking primers each encompassed a BstXI restriction site (CCANNNNNTGG) (SEQ ID NO: 28), giving rise to mutually non-compatible overhangs upon enzyme digestion. This special arrangement of restriction sites enabled a particularly efficient ligation and cloning of the synthetic gene. Substitution of the amino acid Gln28 to His with respect to the original Lcn2 sequence was necessary to introduce the first BstXI site, while the second one naturally occurs in the cDNA of Lcn2. Furthermore, the unpaired residue Cys87 was replaced by Ser during the gene assembly. After one pot PCR the resulting gene fragment was inserted into a vector providing the missing parts of the Lcn2 structural gene. This illustration also depicts two short primers (SEQ ID NO: 32 and SEQ ID NO: 33) upstream and downstream, respectively, of the cassette flanked by the two BstXI restriction sites, which served for double stranded DNA sequencing. FIG. 1 discloses SEQ ID NOS 24, 32, 16, 33, 35, 34, 36, 37, 21, 18, 19, 22, 38, 25, and 39, top to bottom, left to right, respectively, in order of appearance. Figure also discloses Strep-Tag™ as SEQ ID NO: 40.

FIG. 2 illustrates the nucleotide sequence of a library of synthetic Lcn2 genes (only the central cassette flanked by the two BstXI restriction sites, as in FIG. 1, is shown). This gene fragment was prepared by Sloning BioTechnology GmbH. Compared with the DNA library described in FIG. 1 there are two differences. First, whenever possible, codons optimized for *E. coli* expression were used throughout for the non-mutated amino acid positions. Second, a mixture of 19 different triplets (GAC, TTC, CTG, CAC, AAT, AGC, ACC, GCA, ATG, CCT, GTT, TGG, GAG, CAA, ATC, GGA, CGT, GCA, TAC), each encoding a different amino acid except Cysteine, was employed at the 20 randomized positions, which are identical to the ones depicted in FIG. 1. Numbering of amino acids corresponds here to an internal scheme employed by Sloning BioTechnology GmbH, whereby Gly No. 1 is the first amino acid codon directly following the upstream BstX1 restriction site. FIG. 2 discloses SEQ ID NOS 41, 43, and 42, respectively, in order of appearance.

Figure 3A:
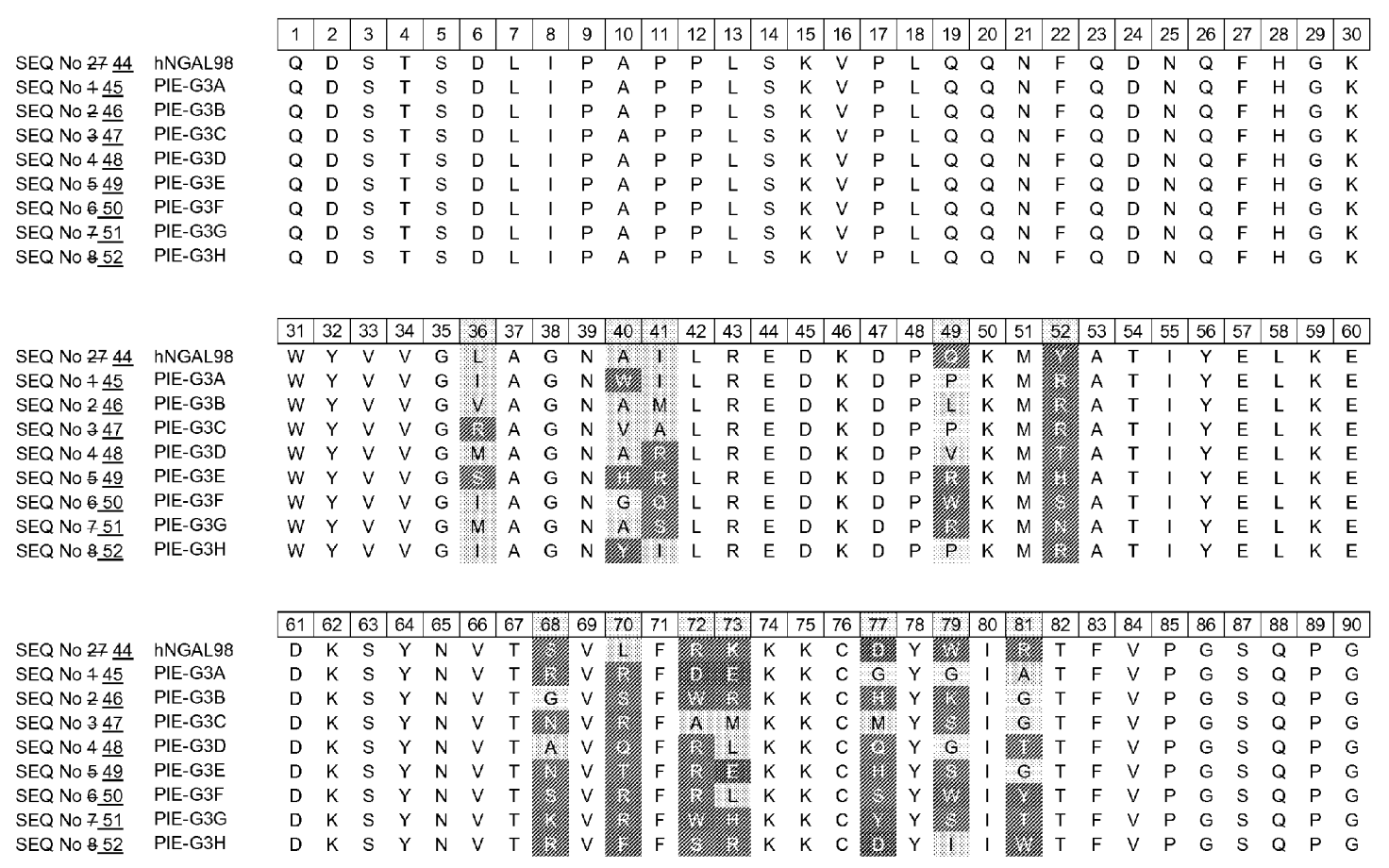

FIGS. 3A-3B depicts an alignment of certain amino acid sequences of Glypican-3-specific, NGAL-based lipocalin muteins in comparison with the polypeptide sequence of wildtype NGAL lipocalin. The NGAL-derived, Glypican-3 binding muteins comprise residues 1 to 178, meaning they have the length of the mature wildtype proteins. Residues 179 to 188 are the sequence of a streptavidin binding tag, Strep-Tag™, used in the isolation of generated muteins. Alignment discloses full-length sequences including Strep-Tag™ as SEQ ID NOS 44-52, respectively, in order of appearance. Figure also discloses Strep-Tag™ as SEQ ID NO: 40.

FIG. 5 depicts the results of a competitive binding assay of selected Lcn2 muteins.

FIG. 6 depicts the affinities of selected muteins for human Glypican-3 as determined by surface-plasmon-resonance (SPR).

FIG. 7 depicts the results of a cell-based binding assays of selected Lcn2 muteins for human, cynomolgus, and mouse GPC3 transfected SK-Hep1 cells.

FIG. 8 depicts the amino acid sequence of SEQ ID NO:27.

DETAILED DESCRIPTION OF THE INVENTION

Figure 3B:
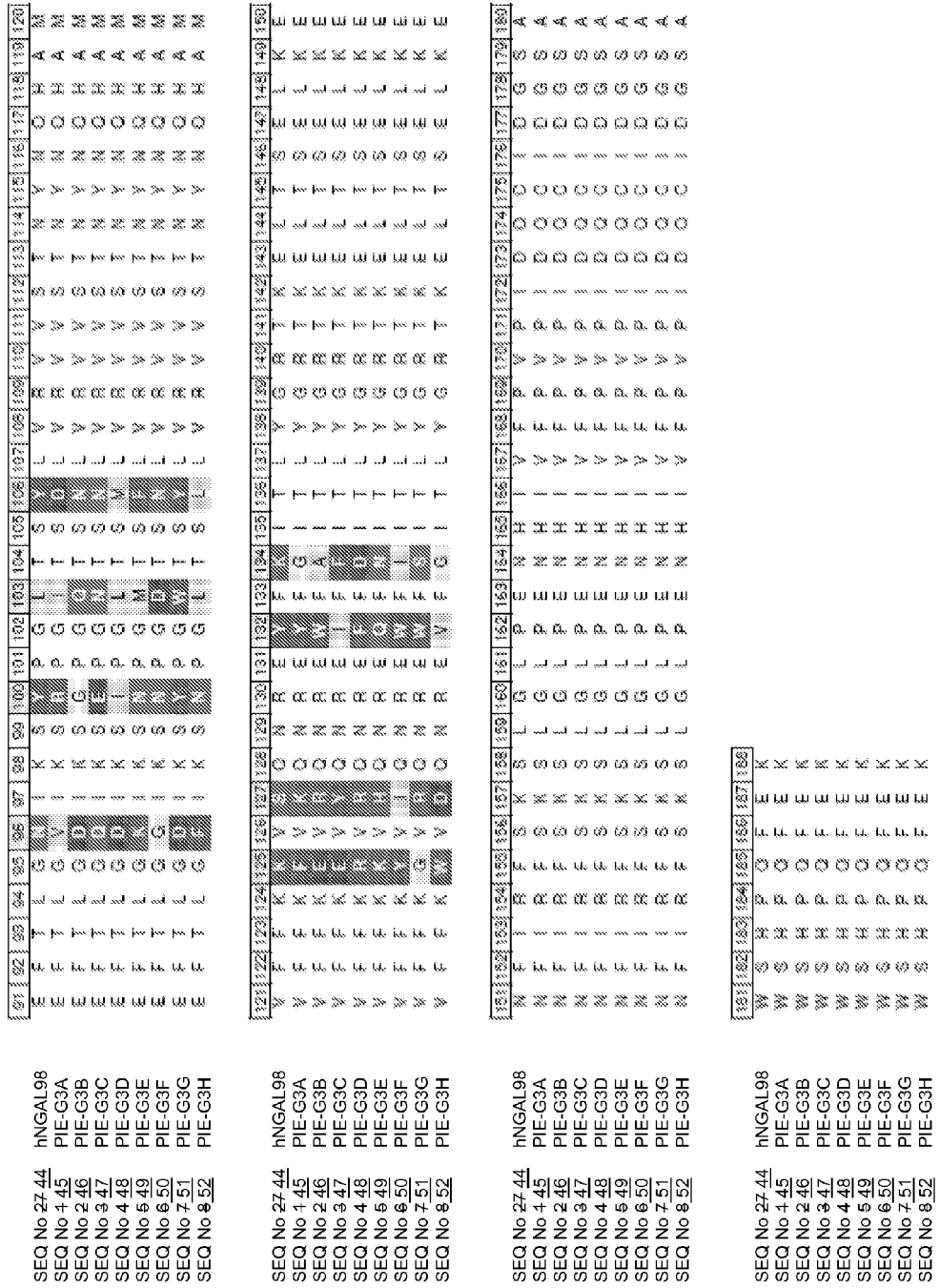

In one aspect, the present invention relates to novel, specific-binding proteins directed against or specific for Glypican-3 (GPC3). Proteins of the invention may be used for therapeutic and/or diagnostic purposes. A protein of the invention includes particularly a lipocalin mutein, also designated herein as "mutein of a lipocalin" or "anticalin". More preferably, a protein of the invention is a hNGAL mutein as described herein. As used herein, a protein of the invention "specifically binds" a target (here, GPC3) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

Likewise, in another aspect, the invention relates to a lipocalin mutein, wherein said mutein comprises at one or more positions corresponding to position 36, 40, 41, 49, 52, 68, 70, 72, 73, 77, 79, 81, 96, 100, 103, 106, 125, 127, 132, and/or 134 of the linear polypeptide sequence of hLcn2 (SEQ ID NO:27) a substitution, preferably a substitution as described herein.

In an alternative aspect, the invention relates to a polypeptide comprising a lipocalin, preferably hNGAL shown in SEQ ID NO:27, wherein the hNGAL comprises at 1, 2, 3, 4, 5, 6, 7, 8, 9, 10, 11, 12, 13, 14, 15, 16, 17, 18, 19, or 20 amino acid positions corresponding to positions 36, 40, 41, 49, 52, 68, 70, 72, 73, 77, 79, 81, 96, 100, 103, 106, 125, 127, 132, and/or 134 of the linear polypeptide sequence of hLcn2 (SEQ ID NO:27) a substitution, preferably a substitution as described herein. The polypeptide of said alternative aspect is preferably an anticalin.

Similarly, the invention relates to a lipocalin mutein derived from NGAL having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind GPC3 as given non-natural target with detectable affinity. Advantageously, the lipocalin mutein comprises at 1, 2, 3, 4, 5, 6, 7, 8, 9, 10, 11, 12, 13, 14, 15, 16, 17, 18, 19 or 20 amino acid position(s) corresponding to the amino acid at position 36, 40, 41, 49, 52, 68, 70, 72, 73, 77, 79, 81, 96, 100, 103, 106, 125, 127, 132, and/or 134 of the linear polypeptide sequence of NGAL (SEQ ID NO: 27) a substitution, preferably a substitution as described herein.

The term "position" when used in accordance with the invention means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids. Accordingly, the position of a given amino acid in accordance with the invention which may be substituted may very due to deletion or addition of amino acids elsewhere in a (mutant or wild-type) lipocalin. Similarly, the position of a given nucleotide in accordance with the present invention which may be substituted may vary due to deletions or additional nucleotides elsewhere in a mutein or wild type lipocalin 5'-untranslated region (UTR) including the promoter and/or any other regulatory sequences or gene (including exons and introns).

Thus, under a "corresponding position" in accordance with the invention it is preferably to be understood that nucleotides/amino acids may differ in the indicated number but may still have similar neighboring nucleotides/amino acids. Said nucleotides/amino acids which may be exchanged, deleted or added are also comprised by the term "corresponding position".

Specifically, in order to determine whether a nucleotide residue or amino acid residue of the amino acid sequence of a lipocalin different from a NGAL lipocalin mutein of the invention corresponds to a certain position in the nucleotide sequence or the amino acid sequence of a NGAL lipocalin mutein as described, in particular any of SEQ ID NOs: 1-8 or that having one or more amino acid substitutions at position 36, 40, 41, 49, 52, 68, 70, 72, 73, 77, 79, 81, 96, 100, 103, 106, 125, 127, 132, and/or 134 of the linear polypeptide sequence of NGAL (SEQ ID NO: 27), a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a lipocalin mutein of any of SEQ ID Nos: 1-8 or that having one or more amino acid substitutions at position 36, 40, 41, 49, 52, 68, 70, 72, 73, 77, 79, 81, 96, 100, 103, 106, 125, 127, 132, and/or 134 of the linear polypeptide sequence of NGAL (SEQ ID NO: 27) can serve as "subject sequence", while the amino acid sequence of a lipocalin different from NGAL serves as "query sequence".

Given the above, a skilled artisan is thus readily in a position to determine which amino acid position mutated in Lcn2 as described herein corresponds to an amino acid of a scaffold other than Lcn2, preferably such as one of those described herein. Specifically, a skilled artisan can align the amino acid sequence of a mutein as described herein, in particular a NGAL mutein (or anticalin) of the invention with the amino acid sequence of a different lipocalin to determine which amino acid(s) of said mutein correspond(s) to the respective amino acid(s) of the amino acid sequence of said different lipocalin. More specifically, a skilled artisan can thus determine which amino acid of the amino acid sequence of said different lipocalin corresponds to the amino acid at position(s) 36, 40, 41, 49, 52, 68, 70, 72, 73, 77, 79, 81, 96, 100, 103, 106, 125, 127, 132, and/or 134 of the linear polypeptide sequence of hLcn2 (SEQ ID NO:27).

Proteins of the invention, which are directed against or specific for GPC3, include any number of specific-binding protein muteins that are based on a defined protein scaffold. As used herein, a "mutein," a "mutated" entity (whether protein or nucleic acid) or "mutant" refers to the exchange, deletion, or insertion of one or more nucleotides or amino acids, respectively, compared to the naturally occurring (wild-type) nucleic acid or protein "reference" scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50. However, it is preferred that a mutein of the invention is still capable of binding GPC3.

A protein of the invention can be a mutein of a lipocalin, preferably a lipocalin selected from the group consisting of retinol-binding protein (RBP), bilin-binding protein (BBP), apolipoprotein D (APO D), neutrophil gelatinase associated lipocalin (NGAL), tear lipocalin (TLPC), $\alpha_2$-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1), with NGAL being a preferred lipocalin. As used herein, a "lipocalin" is defined as monomeric protein of approximately 18-20 kDA in weight, having a cylindrical b-pleated sheet supersecondary structural region comprising a plurality of (preferably eight) b-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%)

yet retaining a highly conserved overall folding pattern. The correspondence between positions in various lipocalins is well known to one of skill in the art. See, for example, U.S. Pat. No. 7,250,297.

In a preferred embodiment, a protein of the invention is a mutein of Lipocalin 2 (Lcn 2; also known as human neutrophil gelatinase-associated lipocalin, hNGAL, or as siderocalin). The term "human neutrophil gelatinase-associated lipocalin" or "hNGAL" or "lipocalin 2" or "Lcn2" as used herein refers to the mature hNGAL with the SWISS-PROT/UniProt Data Bank Accession Number P80188 (Isoform 1). The amino acid sequence shown in SWISS-PROT/UniProt Data Bank Accession Number P80188 is preferred as a "reference sequence".

Most preferred, the amino acid sequence shown in SEQ ID NO:27 (also shown in FIG. 8) is preferred as a "reference sequence". SEQ ID NO:27 shows the mature hNGAL. The terms "reference sequence" and "wild type sequence" (of NGAL) are used interchangeably herein. The mature form of this protein has amino acids 21 to 198 of the complete sequence, since a signal peptide of amino acids 1-20 (MPLGLLWLGL ALLGALHAQA) (SEQ ID NO: 29) is cleaved off. The protein further has a disulfide bond formed between the amino acid residues at positions 76 and 175 of the mature protein.

Generally, when referred to herein a "mutein of a lipocalin" or "lipocalin mutein", in particular a "mutein of Lipocalin 2" or "Lipocalin 2 mutein" of the invention can also be designated as "anticalin". Accordingly, these terms can be equally used herein. Preferably, an anticalin is different from its naturally occurring counterpart lipocalin in that it differs in at least one amino acid from its naturally occurring counterpart lipocalin. The difference might be an amino acid substitution, deletion and/or addition, with a substitution being preferred. Preferably, an anticalin of the invention differs in at least 1, 2, 3, 4, 5, 6, 7, 8, 9, 10, 11, 12, 13, 14, 15, 16, 17, 18, 19 or 20 or even more amino acid position(s), preferably at the amino acid positions as described herein.

In this context, the inventors identified a specific group of Lipocalin 2 muteins with mutations at specific positions which show detectable affinity as well as specificity for GPC3. Suitable amino acid positions for mutation include sequence positions 36, 40, 41, 49, 52, 68, 70, 72, 73, 77, 79, 81, 96, 100, 103, 106, 125, 127, 132, and/or 134, of the linear polypeptide sequence of human Lipocalin 2 (SEQ ID NO:27). The present invention also relates to nucleic acids encoding these proteins.

Other protein scaffolds that can be engineered in accordance with the present invention to provide protein muteins that bind GPC3 with detectable affinity include: an EGF-like domain, a Kringle-domain, a fibronectin type I domain, a fibronectin type II domain, a fibronectin type III domain, a PAN domain, a Gla domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (Ill. et al. "Design and construction of a hybrid immunoglobulin domain with properties of both heavy and light chain variable regions" Protein Eng 10:949-57 (1997)), "Minibodies" (Martin et al. "The affinity-selection of a minibody polypeptide inhibitor of human interleukin-6" EMBO J 13:5303-9 (1994)), "Diabodies" (Holliger et al. "Diabodies': small bivalent and bispecific antibody fragments" PNAS USA 90:6444-6448 (1993)), "Janusins" (Traunecker et al. "Bispecific single chain molecules (Janusins) target cytotoxic lymphocytes on HIV infected cells" EMBO J 10:3655-3659 (1991) and Traunecker et al. "Janusin: new molecular design for bispecific reagents" Int J Cancer Suppl 7:51-52 (1992), a nanobody, an adnectin, a tetranectin, a microbody, an affilin, an affibody an ankyrin, a crystallin, a knottin, ubiquitin, a zinc-finger protein, an autofluorescent protein, an ankyrin or ankyrin repeat protein or a leucine-rich repeat protein, an avimer (Silverman, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P 2005, Nat Biotech, December; 23(12):1556-61, E-Publication in Nat. Biotech. 2005 November 20 edition); as well as multivalent avimer proteins evolved by exon shuffling of a family of human receptor domains as also described in Silverman J, Lu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P, Nat Biotech, December; 23(12):1556-61, E-Publication in Nat. Biotechnology. 2005 November 20 edition).

A protein of the invention may include the wild type (natural) amino acid sequence of the "parental" protein scaffold (such as a lipocalin) outside the mutated amino acid sequence positions; alternatively, a lipocalin mutein may also contain amino acid mutations outside the sequence positions subjected to mutagenesis that do not interfere with the binding activity and the folding of the mutein. Such mutations can be accomplished on a DNA level using established standard methods (Sambrook, J. et al. (2001) *Molecular Cloning: A Laboratory Manual*, 3rd Ed., Cold Spring Harbor Laboratory Press, Cold Spring Harbor, N.Y.). Possible alterations of the amino acid sequence are insertions or deletions as well as amino acid substitutions.

Such substitutions may be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. One the other hand, it is also possible to introduce non-conservative alterations in the amino acid sequence. In addition, instead of replacing single amino acid residues, it is also possible to either insert or delete one or more continuous amino acids of the primary structure of a parental protein scaffold, where these deletions or insertion result in a stable folded/functional mutein, which can be readily tested by the skilled worker.

The skilled worker will appreciate methods useful to prepare protein muteins contemplated by the present invention but whose protein or nucleic acid sequences are not explicitly disclosed herein. As an overview, such modifications of the amino acid sequence include, e.g., directed mutagenesis of single amino acid positions in order to simplify subcloning of a mutated lipocalin gene or its parts by incorporating cleavage sites for certain restriction enzymes. In addition, these mutations can also be incorporated to further improve the affinity of a lipocalin mutein for a given target. Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

Accordingly, the invention also includes functional variants of proteins disclosed herein, which have a threshold sequence identity or sequence homology to a reference protein. By "identity" or "sequence identity" is meant a property of sequences that measures their similarity or relationship. The term "sequence identity" or "identity" as used in the present invention means the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins.

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

It is also possible to deliberately mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages. With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild type sequence of hNGAL. In some embodiments where a human Lipocalin 2 mutein of the invention has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein.

In some embodiments, a protein according to the invention binds GPC3 with a $K_D$ of 100 µM or less, including 5 µM or less, about 500 nM, about 200 nM or less, 100 nM or less, 10 nM or less, 1 nM or less, 0.5 nM or less, 0.3 nM or less, or 0.2 nM or less. A protein of the invention may specifically bind one or more continuous, discontinuous or conformation epitope(s) of the mature, folded bioactive form of GPC3.

A protein of the invention preferably binds to GPC3 with an affinity by a $K_D$ of about 10 nM. Binding affinities have been found by the present inventors to often be of a $K_D$ of about 1 nM and, in some cases, about 0.3 or 0.2 nM and below.

The binding affinity of a protein of the invention (e.g. a mutein of a lipocalin) to a selected target (in the present case, GPC3), can be measured (and thereby $K_D$ values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

The amino acid sequence of a protein of the invention may have a high sequence identity to mature human Lipocalin 2 or other lipocalins. In this context, a protein of the invention may have at least 70%, at least 75%, at least 80%, at least 82%, at least 85%, at least 87%, at least 90% identity, including at least 95% identity to a protein selected from the group consisting of the sequence of SEQ ID NOS: 1-8 and SEQ ID NO:27.

The invention also includes structural homologues of the proteins selected from the group consisting of the sequence of SEQ ID NOS: 1-8, which have an amino acid sequence homology or sequence identity of more than about 60%, preferably more than 65%, more than 70%, more than 75%, more than 80%, more than 85%, more than 90%, more than 92% and most preferably more than 95% in relation thereto.

The terms "Glypican-3, "glypican proteoglycan 3," "GPC3, "OTTHUMP00000062492", "GTR2-2" "SGB," "DGSX", "SDYS", "SGBS", "OCI-5", and, "SGBSI" are used interchangeably, and include variants, isoforms and species homologs of human Glypican-3. The complete amino acid sequence of an exemplary human Glypican-3 has Genbank/NCBI accession number NM_004484.

In line with the above, a protein of the invention preferably acts as an antagonist of GPC3. In some embodiments, a protein of the invention (e.g., a human Lipocalin 2 mutein) may act as an antagonist of GPC3 by inhibiting the ability of the GPC3 molecule to bind to or otherwise interact with its cognate ligand.

In yet another aspect, the present invention includes various lipocalin muteins, including muteins of human Lipocalin 2 that specifically bind GPC3. In this sense, GPC3 can be regarded a non-natural ligand of wild type human Lipocalin 2, where "non-natural ligand" refers to a compound that does not bind to wildtype lipocalins, including human Lipocalin 2 under physiological conditions. By engineering wildtype lipocalins such as human Lipocalin 2 with mutations at certain positions, the present inventors have demonstrated that high affinity and high specificity for a non-natural ligand is possible. In one aspect at least at 1, 2, 3, 4, 5, 6, 7, 8, 9, 10, 11, 12, 13, 14, 15, 16, 17, 18, 19, and/or 20 nucleotide triplet(s) encoding for any of the sequence positions 36, 40, 41, 49, 52, 68, 70, 72, 73, 77, 79, 81, 96, 100, 103, 106, 125, 127, 132, and/or 134 of the linear polypeptide sequence of hLcn2 (SEQ ID NO:27), or other parallel sites on lipocalins, a random mutagenesis can be carried out by allowing substitution at this positions by a subset of nucleotide triplets.

Further, the lipocalins can be used to generate muteins that have a mutated amino acid residue at any one or more, including at least at any two, three, four, five, six, seven, eight, nine, ten, eleven, twelve, thirteen, fourteen, fifteen, sixteen, seventeen, eighteen, nineteen or twenty, of the sequence positions of the sequence positions corresponding to the sequence positions 36, 40, 41, 49, 52, 68, 70, 72, 73, 77, 79, 81, 96, 100, 103, 106, 125, 127, 132, and 134 of the linear polypeptide sequence of a mature human Lipocalin 2.

A substitution at sequence position 36 may for example be a substitution Leu 36→Ile, Val, Arg, Met or Ser. A substitution at sequence position 40 may for example be a substitution Ala 40→Trp, Val, His, Gly or Tyr. A substitution at sequence position 41 may for example be a substitution Ile 41→Met, Ala, Arg, Gln, or Ser. A substitution at sequence position 49 may for example be a substitution Gln 49→Pro, Leu, Val, Arg or Trp. A substitution at sequence position 52 may for example be a substitution Tyr 52→Arg, Thr, His, Ser or Asn. A substitution at sequence position 68 may for example be a substitution Ser 68→Arg, Gly, Asn, Ala, or Lys. A substitution at sequence position 70 may for example be a substitution Leu 70→Arg, Ser, Gln, Thr or Phe. A substitution at sequence position 72 may for example be a substitution Arg 72→Asp, Trp, Ala, or Ser. A substitution at sequence position 73 may for example be a substitution Lys 73→Glu, Arg, Met, Leu or His. A substitution at sequence position 77 may for example be a substitution Asp 77→Gly, His, Met, Gln, Ser or Tyr. A substitution at sequence position 79 may for example be a substitution Trp 79→Gly, Lys, Ser or Ile. A substitution at sequence position 81 may for example be a substitution Arg 81→Ala, Gly, Thr, Tyr or Trp. A substitution at sequence position 96 may for example be a substitution Asn 96→Val, Asp, Gln, Lys, Gly or Phe. A substitution at sequence position 100 may for example be a substitution Tyr 100→Arg, Gly, Glu, Ile or Asn. A substitution at sequence position 103 may for example be a substitution Leu 103→Ile, Gln, Asn, Met, Asp, or Trp. A substitution at sequence position 106 may for example be a substitution Tyr 106→Asp, Asn, Met, Phe, Asn or Leu. A substitution at sequence position 125 may for example be a substitution Lys 125→Phe, Glu, Arg, Tyr, Gly or Trp. A substitution at sequence position 127 may for example be a substitution Ser 127→Lys, Arg, Tyr, His, Ile or Asp. A substitution at sequence position 132 may for example be a substitution Tyr 132→Trp, Ile, Phe, Gln or Val. A substitution at sequence position 134 may for example be a substitution Lys 134→Gly, Ala, Phe, Asp, Asn, Ile or Ser. Noteworthy, any of the amino acids that substitutes the corresponding amino acid in the reference sequence can be exchanged by a corresponding conservative amino acid. In particular, conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan.

In one embodiment, a mutein of the invention, which binds to GPC3 includes the following amino acid replacements:
(a) Leu 36→Ile; Ala 40→Trp; Gln 49→Pro; Tyr 52→Arg; Ser 68→Arg; Leu 70→; Arg 72→Asp; Lys 73→Glu; Asp 77→Gly; Trp 79→Gly; Arg 81→Ala; Asn 96→Val; Tyr 100→Arg; Leu 103→Ile; Tyr 106→Asp; Lys 125→Phe; Ser 127→Lys; Lys 134→Gly;
(b) Leu 36→Val; Ile 41→Met; Gln 49→Leu; Tyr 52→Arg; Ser 68→Gly; Leu 70→Ser; Arg 72→Trp; Lys 73→Arg; Asp 77→His; Trp 79→Lys; Arg 81→Gly; Asn 96→Asp; Tyr 100→Gly; Leu 103→Gln; Tyr 106→Asn; Lys 125→Glu; Ser 127→Arg; Tyr 132→Trp; Lys 134→Ala;
(c) Leu 36→Arg; Ala 40→Val; Ile 41→Ala; Gln 49→Pro; Tyr 52→Arg; Ser 68→Asn; Leu 70→Arg; Arg 72→Ala; Lys 73→Met; Asp 77→Met; Trp 79→Ser; Arg 81→Gly; Asn 96→Gln; Tyr 100→Glu; Leu 103→Asn; Tyr 106→Asn; Lys 125→Glu; Ser 127→Tyr; Tyr 132→Ile; Lys 134→Phe;
(d) Leu 36→Met; Ile 41→Arg; Gln 49→Val; Tyr 52→Thr; Ser 68→Ala; Leu 70→Gln; Lys 73→Leu; Asp 77→Gln; Trp 79→Gly; Arg 81→Thr; Asn 96→Asp; Tyr 100→Ile; Tyr 106→Met; Lys 125→Arg; Ser 127→Arg; Tyr 132→Phe; Lys 134→Asp;
(e) Leu 36→Ser; Ala 40→His; Ile 41→Arg; Gln 49→Arg; Tyr 52→His; Ser 68→Asn; Leu 70→Thr; Lys 73→Glu; Asp 77→His; Trp 79→Ser; Arg 81→Gly; Asn 96→Lys; Tyr 100→Asn; Leu 103→Met; Tyr 106→Phe; Ser 127→His; Tyr 132→Gln; Lys 134→Asn;
(f) Leu 36→Ile; Ala 40→Gly; Ile 41→Gln; Gln 49→Trp; Tyr 52→Ser; Leu 70→Arg; Lys 73→Leu; Asp 77→Ser; Arg 81→Tyr; Asn 96→Gly; Tyr 100→Asn; Leu 103→Asp; Tyr 106→Asn; Lys 125→Tyr; Ser 127→Ile; Tyr 132→Trp; Lys 134→Ile;
(g) Leu 36→Met; Ile 41→Ser; Gln 49→Arg; Tyr 52→Asn; Ser 68→Lys; Leu 70→Arg; Arg 72→Trp; Lys 73→His; Asp 77→Tyr; Trp 79→Ser; Arg 81→Thr; Asn 96→Asp; Leu 103→Trp; Lys 125→Gly; Ser 127→Arg; Tyr 132→Trp; Lys 134→Ser;
(h) Leu 36→Ile; Ala 40→Tyr; Gln 49→Pro; Tyr 52→Arg; Ser 68→Arg; Leu 70→Phe; Arg 72→Ser; Lys 73→Arg; Trp 79→Ile; Arg 81→Trp; Asn 96→Phe; Tyr 100→Asn; Tyr 106→Leu; Lys 125→Trp; Ser 127→Asp; Tyr 132→Val; Lys 134→Gly.

The numbering is preferably in relation to the linear polypeptide sequence of NGAL (SEQ ID NO: 27). Accordingly, given the teaching of the invention as described above, a skilled artisan can readily determine which amino acids in a lipoprotein correspond to those described above in (a) to (h) in the preferred reference sequence of NGAL (SEQ ID NO: 27) so as to mutate said amino acids in said lipoprotein.

It is also noted that the complex formation between the respective mutein and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective mutein and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

In one embodiment, the muteins disclosed herein can be linked, either N- or C-terminal to a fusion partner which is preferably a protein, or a protein domain or a peptide. Examples of a fusion partner is an affinity tag such as pentahistidine tag (SEQ ID NO: 30), a hexahistidine tag (SEQ ID NO: 31) or a steptavidin tag (e.g. Streptag®). Thus, the present application encompasses also all explicitly and generic described muteins equipped with such tags.

The term "fragment" as used in the present invention in connection with the feature lipocalin mutein fragment relates to proteins or peptides derived from full-length mature Lcn 2 that are N-terminally and/or C-terminally shortened, i.e. lacking at least one of the N-terminal and/or C-terminal amino acids. Such fragments include preferably at least 10, more preferably 20, most preferably 30 or more consecutive amino acids of the primary sequence of mature Lcn 2 and are usually detectable in an immunoassay of mature Lcn 2. The word "detect" or "detecting" as used herein is understood both on a quantitative and a qualitative level, as well as a combination thereof. It thus includes quantitative, semi-quantitative and qualitative measurements of a molecule of interest. Accordingly, the presence or absence of a molecule such as GPC3, e.g. in a sample, as well as its concentration or level may be determined.

Also included in the scope of the present invention are the above muteins, which have been altered with respect to their immunogenicity, to reduce any detected immunogenicity by employing methods known to the skilled worker in the field.

Cytotoxic T-cells recognize peptide antigens on the cell surface of an antigen-presenting cell in association with a class I major histocompatibility complex (MHC) molecule. The ability of the peptides to bind to MHC molecules is allele specific and correlates with their immunogenicity. To reduce the immunogenicity of a given protein, the ability to predict which peptides in a protein have the potential to bind to a given MHC molecule is of great value. Approaches that employ a computational threading approach to identify potential T-cell epitopes have been previously described to predict the binding of a given peptide sequence to MHC class I molecules (Altuvia et al. (1995) *J. Mol. Biol.* 249: 244-250). Such an approach may also be utilized to identify potential T-cell epitopes in the muteins of the invention and to make, depending on its intended use, a selection of a specific mutein on the basis of its predicted immunogenicity. It may be furthermore possible to subject peptide regions that have been predicted to contain T-cell epitopes to additional mutagenesis to reduce or eliminate these T-cell epitopes and thus minimize immunogenicity. The removal of amphipathic epitopes from genetically engineered antibodies has been described (Mateo et al. (2000) *Hybridoma* 19(6):463-471) and may be adapted to the muteins of the present invention. The muteins thus obtained may possess a minimized immunogenicity, which is desirable for their use in therapeutic and diagnostic applications, such as those described below.

For some applications, it is also useful to employ the muteins of the invention in a conjugated form. The conjugation can be carried out using any conventional coupling method known in the art.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

In general, it is possible to label a lipocalin mutein described herein with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation. Alkaline phosphatase, horseradish peroxidase or β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the muteins of the present invention. The muteins of the invention may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). Examples of suitable toxins include, but are not limited to pertussis-toxin, diphtheria toxin, ricin, saporin, pseudomonas exotoxin, calicheamicin or a derivative thereof, a taxoid, a maytansinoid, a tubulysin or a dolastatin analogue. The dolastatin analogue may be auristatin E, monomethylauristatin E, auristatin PYE and auristatin PHE. Examples of cytostatic agent include, but are not limited to Cisplatin, Carboplatin, Oxaliplatin, 5-Fluorouracil, Taxotere (Docetaxel), Paclitaxel, Anthracycline (Doxorubicin), Methotrexate, Vinblastin, Vincristine, Vindesine, Vinorelbine, Dacarbazine, Cyclophosphamide, Etoposide, Adriamycine, Camptotecine, Combretatastin A-4 related compounds, sulfonamides, oxadiazolines, benzo[b]thiophenessynthetic spiroketal pyrans, monotetrahydrofuran compounds, curacin and curacin derivatives, methoxyestradiol derivatives and Leucovorin. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

In one embodiment, the muteins of the invention may also be coupled to a targeting moiety that targets a specific body region in order to deliver the inventive muteins to a desired region or area within the body. One example wherein such modification may be desirable is the crossing of the blood-brain-barrier. In order to cross the blood-brain barrier, the muteins of the invention may be coupled to moieties that facilitate the active transport across this barrier (see Gaillard P J, et al. (2005) *International Congress Series.* 1277, 185-198 or Gaillard P J, et al. (2005) *Expert Opin Drug Deliv.* 2(2), 299-309). Such compounds are for example available under the trade name 2B-Trans™ (to-BBB technologies BV, Leiden, NL). Other exemplary targeting molecules to which the muteins of the present invention may be coupled include antibodies, antibody fragments or lipocalin muteins with affinity for a desired target molecule. The target molecule of the targeting moieties may, for example, be a cell-surface antigen. Cell-surface antigens may be specific for a cell or tissue type, such as, for example, cancer cells. Illustrative examples of such cell surface proteins are HER-2 or proteoglycans such as NEU-2.

As indicated above, a mutein of the invention may in some embodiments be conjugated to a compound that extends the serum half-life of the mutein (in this regard see also PCT publication WO 2006/56464 where such conjugation strategies are described with references to muteins of human neutrophil gelatinase-associated lipocalin with binding affinity for CTLA-4). The compound that extends the serum half-life may be a polyalkylene glycol molecule, such as polyethylene (PEG) or an activated derivative thereof; hydroxyethyl starch, fatty acid molecules, such as palmitic acid (Vajo & Duckworth (2000) *Pharmacol. Rev.* 52, 1-9), an Fc part of an immunoglobulin, a $C_H3$ domain of an immunoglobulin, a $C_H4$ domain of an immunoglobulin, albumin or a fragment thereof, an albumin binding peptide, an albumin binding protein, transferrin, or the tag Pro-Ala-Ser, to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation compounds for extending the half-life of a lipocalin mutein of the invention include albumin (Osborn et al. (2002) *J. Pharmacol. Exp. Ther.* 303, 540-548), or an albumin binding protein, for example, a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis et al. (2002) *J. Biol. Chem.* 277, 35035-35043).

In other embodiments, albumin itself or a biological active fragment of albumin can be used as compound of a lipocalin mutein of the invention that extends the serum half-life of the mutein. The term "albumin" includes all mammal albumins such as human serum albumin or bovine serum albumin or rat albumin. The albumin or fragment thereof can be recombinantly produced as described in U.S. Pat. No. 5,728,553 or European patent applications EP 0 330 451 and EP 0 361 991. Recombinant human albumin (Recombumin®) for use as a protein stabilizer is for example available from Novozymes Delta Ltd. (Nottingham, UK).

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

Using transferrin as a moiety to extend the serum half-life of the muteins of the invention, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer is also commercially available from Novozymes Delta Ltd. (Nottingham, UK).

If an Fc part of an immunoglobulin is used for the purpose to prolong the serum half-life of the muteins of the invention, the SynFusion™ technology, commercially available from Syntonix Pharmaceuticals, Inc (MA, USA), may be used. The use of this Fc-fusion technology allows the creation of longer-acting biopharmaceuticals and may for example comprise two copies of the mutein linked to the Fc region of an antibody to improve pharmacokinetics, solubility, and production efficiency.

Yet another alternative to prolong the half-life of a mutein of the invention is to fuse the N- or C-terminus of a mutein of the invention to long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as compound that extends the half-life of the mutein, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) "The Clinical Efficacy of Poly(Ethylene Glycol)-Modified Proteins" *J. Control. Release* 11, 139-148). The molecular weight of such a polymer, preferrably polyethylene glycol, may range from about 300 to about 70.000 Dalton, including, for example, polyethylene glycol with a molecular weight of about 10.000, of about 20.000, of about 30.000 or of about 40.000 Dalton. Moreover, e.g. as described in U.S. Pat. No. 6,500,930 or 6,620,413, carbohydrate oligo- and polymers such as starch or hydroxyethyl starch (HES) can be conjugated to a mutein of the invention for the purpose of serum half-life extension.

In another embodiment, in order to provide suitable amino acid side chains for conjugating one of the above compounds to the muteins of the invention artificial amino acids may be introduced by mutagenesis. Generally, such artificial amino acids are designed to be more reactive and thus to facilitate the conjugation to the desired moiety. One example of such an artificial amino acid that may be introduced via an artificial tRNA is para-acetyl-phenylalanine.

For several applications of the muteins disclosed herein, it may be advantageous to use them in the form of fusion proteins. In some embodiments, the inventive mutein is fused at its N-terminus and/or it's C-terminus to a protein, a protein domain or a peptide such as a signal sequence and/or an affinity tag.

For pharmaceutical applications, a mutein of the invention may be fused to a fusion partner that extends the in vivo serum half-life of the mutein (see again PCT publication WO 2006/56464 where suitable fusion partner are described with references to muteins of human neutrophile gelatinase-associated lipocalin with binding affinity for CTLA-4). Similar to the conjugated compounds described above, the fusion partner may be an Fc part of an immunoglobulin, a C$_H$3 domain of an immunoglobulin, a C$_H$4 domain of an immunoglobulin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a lipocalin mutein of the invention include albumin (Osborn, B. L. et al. (2002) supra *J. Pharmacol. Exp. Ther.* 303, 540-548), or an albumin binding protein, for example, a bacterial albumin binding domain, such as streptococcal protein G (König, T. and Skerra, A. (1998) supra *J. Immunol. Methods* 218, 73-83). The albumin binding peptides described in Dennis et al, supra (2002) or US patent application 2003/0069395 having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr can also be used as fusion partner. It is also possible to use albumin itself or a biological active fragment of albumin as fusion partner of a lipocalin mutein of the invention. The term "albumin" includes all mammal albumins such as human serum albumin or bovine serum albumin or rat serum albumin. The recombinant production of albumin or fragments thereof is well known in the art and for example described in U.S. Pat. No. 5,728,553, European patent application EP 0 330 451 or EP 0 361 991.

The fusion partner may confer new characteristics to the inventive lipocalin mutein such as enzymatic activity or binding affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins," cf.

Schlehuber, S., and Skerra, A. (2001), Duocalins, engineered ligand-binding proteins with dual specificity derived from the lipocalin fold (*Biol. Chem.* 382, 1335-1342), or toxins.

In particular, it may be possible to fuse a lipocalin mutein of the invention with a separate enzyme active site such that both "components" of the resulting fusion protein together act on a given therapeutic target. The binding domain of the lipocalin mutein attaches to the disease-causing target, allowing the enzyme domain to abolish the biological function of the target.

Affinity tags such as the Strep-Tag® or Strep-Tag® II (Schmidt, T. G. M. et al. (1996) *J Mol. Biol.* 255, 753-766), the myc-tag, the FLAG-tag, the His6-tag (SEQ ID NO: 31) or the HA-tag or proteins such as glutathione-S-transferase also allow easy detection and/or purification of recombinant proteins are further examples of preferred fusion partners. Finally, proteins with chromogenic or fluorescent properties such as the green fluorescent protein (GFP) or the yellow fluorescent protein (YFP) are suitable fusion partners for a lipocalin mutein of the invention as well.

The term "fusion protein" as used herein also includes lipocalin muteins according to the invention containing a signal sequence. Signal sequences at the N-terminus of a polypeptide direct this polypeptide to a specific cellular compartment, for example the periplasm of *E. coli* or the endoplasmatic reticulum of eukaryotic cells. A large number of signal sequences is known in the art. A preferred signal sequence for secretion a polypeptide into the periplasm of *E. coli* is the OmpA-signal sequence.

The present invention also relates to nucleic acid molecules (DNA and RNA) comprising nucleotide sequences coding for muteins as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding a functional mutein.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention can include a regulatory sequence, preferably a promoter sequence. In another preferred embodiment, a nucleic acid molecule of the invention includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the invention can also be part of a vector or any other kind of cloning vehicle, such as a plasmid, a phagemid, a phage, a baculovirus, a cosmid or an artificial chromosome such as a YAC or BAC.

The DNA molecule encoding lipocalin muteins of the invention, and in particular a cloning vector containing the coding sequence of such a lipocalin mutein can be transformed into a host cell capable of expressing the gene. Transformation can be performed using standard techniques (Sambrook, J. et al. (2001), supra).

Thus, the invention is also directed to a host cell containing a nucleic acid molecule as disclosed herein.

The invention also relates to a method for the production of a mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eucaryotic host organism and then enriched, purified or isolated from this host organism or its culture. It is also possible to produce a protein in vitro, for example by use of an in vitro translation system. The term "enriched" means that the mutein or a functional fragment thereof constitutes a significantly higher fraction of the total protein present in a sample or solution of interest than in a sample or solution from which it was taken. Enrichment may for instance include the isolation of a certain fraction from a cell extract. This may be obtained by standard techniques such as centrifugation. Examples of other means of enrichment are filtration or dialysis, which may for instance be directed at the removal of undesired molecules below a certain molecular weight, or a precipitation using organic solvents or ammonium sulphate. Purification may for instance include a chromatographic technique, for example gel filtration, ion exchange chromatography, affinity purification, hydrophobic interaction chromatography or hydrophobic charge induction chromatography. Another example for a purification is an electrophoretic technique, such as preparative capillary electrophoresis. Isolation may include the combination of similar methods. As used herein, "substantially pure" or "substantially purified" means a compound or species that is the predominant species present (i.e., on a molar basis it is more abundant than any other individual species in the composition). In some embodiments, a substantially purified composition is a composition in which the species includes at least about 50 percent (on a molar basis) of all molecular or, as applicable, all macromolecular species present. In certain embodiments, a substantially pure composition will have more than about 80%, about 85%, about 90%, about 95%, or about 99% of all molecular or, as applicable, all macromolar species present in the composition.

When producing the mutein in vivo, a nucleic acid encoding a mutein of the invention is introduced into a suitable bacterial or eukaryotic host organism by means of recombinant DNA technology (as already outlined above). For this purpose, the host cell is first transformed with a cloning vector comprising a nucleic acid molecule encoding a mutein of the invention using established standard methods (Sambrook, J. et al. (1989), supra). The host cell is then cultured under conditions, which allow expression of the heterologous DNA and thus the synthesis of the corresponding polypeptide. Subsequently, the polypeptide is recovered either from the cell or from the cultivation medium.

In one aspect, the present invention relates to a method for the generation of a mutein which binds GPC3, comprising:

subjecting a nucleic acid molecule encoding a lipocalin to mutagenesis, resulting in one or more mutein nucleic acid molecule(s).

The method can further include:

expressing the one more mutein nucleic acid molecule(s) obtained in (a) in a suitable expression system, bringing the plurality of muteins into contact with at least a fragment or a mature form of GPC3, and enriching the one or more mutein(s) having a detectable binding affinity for a given target by means of selection and/or isolation.

The term "mutagenesis" as used herein means that the experimental conditions are chosen such that the amino acid naturally occurring at a given sequence position of the lipocalin, including Lcn 2 (hNGAL; Swiss-Prot data bank entry P80188) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

In one non-limiting approach, the coding sequence of human Lipocalin 2 can be used as a starting point for the mutagenesis of the peptide segments selected in the present invention. For the mutagenesis of the recited amino acid positions, the person skilled in the art has at his disposal the various established standard methods for site-directed mutagenesis (Sambrook, J. et al. (2001), supra). A commonly used technique is the introduction of mutations by means of PCR (polymerase chain reaction) using mixtures of synthetic oligonucleotides, which bear a degenerate base composition at the desired sequence positions. Other similar techniques are well known to those of skill in the art.

The nucleic acid molecules defined above can be connected by ligation with the missing 5'- and 3'-sequences of a nucleic acid encoding a lipocalin polypeptide and/or the vector, and can be cloned in a known host organism. A multitude of established procedures are available for ligation and cloning (Sambrook, J. et al. (2001), supra). For example, recognition sequences for restriction endonucleases also present in the sequence of the cloning vector can be engineered into the sequence of the synthetic oligonucleotides. Thus, after amplification of the respective PCR product and enzymatic cleavage the resulting fragment can be easily cloned using the corresponding recognition sequences.

Longer sequence segments within the gene coding for the protein selected for mutagenesis can also be subjected to random mutagenesis via known methods, for example by use of the polymerase chain reaction under conditions of increased error rate, by chemical mutagenesis or by using bacterial mutator strains. Such methods can also be used for further optimization of the target affinity or specificity of a lipocalin mutein. Mutations possibly occurring outside the segments of experimental mutagenesis are often tolerated or can even prove to be advantageous, for example if they contribute to an improved folding efficiency or folding stability of the lipocalin mutein.

In a further embodiment, the method includes subjecting the nucleic acid molecule to mutagenesis at nucleotide triplets coding for at least any 1, 2, 3, 4, 5, 6, 7, 8, 9, 10, 11, 12, 13, 14, 15, 16, 17, 18, 19 or 20 of the sequence positions corresponding to the sequence positions 36, 40, 41, 49, 52, 68, 70, 72, 73, 77, 79, 81, 96, 100, 103, 106, 125, 127, 132, and 134 of the linear polypeptide sequence of the lipocalin, in particular of the linear polypeptide sequence of NGAL (SEQ ID NO: 27). Such a nucleic acid may subjected to mutagenesis and introduced into a suitable bacterial or eukaryotic host organism by using recombinant DNA technology. Obtaining a nucleic acid library of a lipocalin can be carried out using any suitable technique that is known in the art for generating lipocalin muteins with antibody-like properties, i.e. muteins that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255, WO 2005/019256, or WO 2006/56464 for instance. The content of each of these patent applications is incorporated by reference herein in their entirety. After expression of the nucleic acid sequences that were subjected to mutagenesis in an appropriate host, the clones carrying the genetic information for the plurality of respective lipocalin muteins, which bind a given target can be selected from the library obtained. Well known techniques can be employed for the selection of these clones, such as phage display (reviewed in Kay, B. K. et al. (1996) supra; Lowman, H. B. (1997) supra or Rodi, D. J., and Makowski, L. (1999) supra), colony screening (reviewed in Pini, A. et al. (2002) *Comb. Chem. High Throughput Screen.* 5, 503-510), ribosome display (reviewed in Amstutz, P. et al. (2001) *Curr. Opin. Biotechnol.* 12, 400-405) or mRNA display as reported in Wilson, D. S. et al. (2001) *Proc. Natl. Acad. Sci. USA* 98, 3750-3755 or the methods specifically described in WO 99/16873, WO 00/75308, WO 03/029471, WO 03/029462, WO 03/029463, WO 2005/019254, WO 2005/019255, WO 2005/019256, or WO 2006/56464.

In accordance with this disclosure, another embodiment of the above methods comprises:

(i) providing at least a fragment of GPC3 as a given target/ligand for example, contacting the plurality of muteins with said target/ligand in order to allow formation of complexes between said ligand and muteins having binding affinity for said target/ligand, and removing muteins having no or no substantial binding affinity.

In one embodiment of the methods of the invention, the selection binding affinity is carried out under competitive conditions. Competitive conditions as used herein means that selection of muteins encompasses at least one step in which the muteins and the fragment of GPC3 are brought in contact in the presence of an additional ligand, which competes with binding of the muteins to the target (GPC3). Alternatively, the additional ligand competes with binding of the muteins by complexing an epitope distinct from the binding site of the muteins to the target by allosteric effects. Accordingly, any fragment, precursor or mature form of GPC3 can be used in the generation of muteins of the invention.

A further embodiment of the methods of the invention involves operably fusing a nucleic acid coding for the plurality of muteins of the invention and resulting from mutagenesis at the 3' end with a gene coding for the coat protein pIII of a filamentous bacteriophage of the M13-family or for a fragment of this coat protein, in order to select at least one mutein for the binding of a given ligand.

The fusion protein may include additional components such as an affinity tag, which allows the immobilization, detection and/or purification of the fusion protein or its parts. Furthermore, a stop codon can be located between the sequence regions encoding the lipocalin or its muteins and the phage capsid gene or fragments thereof, wherein the stop codon, preferably an amber stop codon, is at least partially translated into an amino acid during translation in a suitable suppressor strain.

For example, the phasmid vector pTLPC27, now also called pTlc27 that is described here can be used for the preparation of a phagemid library encoding muteins of the invention. The inventive nucleic acid molecules coding for muteins of the invention can be inserted into the vector using the two BstXI restriction sites. After ligation a suitable host strain such as *E. coli* XL1-Blue is transformed with the resulting nucleic acid mixture to yield a large number of independent clones. A respective vector can be generated for the preparation of a hyperphagemid library, if desired.

Once a mutein with affinity to a given target has been selected, it is additionally possible to subject such a mutein to another mutagenesis in order to subsequently select variants of even higher affinity or variants with improved properties such as higher thermostability, improved serum stability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation," can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) *J. Mol. Biol.* 255, 589-603. Other methods of random mutagenesis that are suitable for such purposes include random insertion/deletion (RID) mutagenesis as described by Murakami et al. (2002) *Nat. Biotechnol.* 20, 76-81 or nonhomologous random recombination (NRR) as described by Bittker et al. (2002) *Nat. Biotechnol.* 20, 1024-1029. If desired, affinity maturation can also be carried out according to the procedure described in WO 00/75308 or Schlehuber et al. (2000) *J. Mol. Biol.* 297, 1105-1120, where muteins of the bilin-binding protein having high affinity to digoxigenin were obtained. A further approach for improving the affinity is to carry out positional saturation mutagenesis. In this approach "small" nucleic acid libraries can be created in which amino acid exchanges/mutations are only introduced at single positions within any of the four loop segments. These libraries are then directly subjected to a selection step (affinity screening) without further rounds of panning. This approach allows the identification of residues that contribute to improved binding of the desired target and allows identification of "hot spots" that are important for the binding.

In one embodiment, the above method for modifying a mutein further includes introducing a Cys residue at at least one of any of the sequence positions that correspond to sequence positions 14, 21, 60, 84, 88, 116, 141, 145, 143, 146 or 158 of the wild type sequence of human Lipocalin 2 and coupling a moiety that is able to modify the serum half time of said mutein via the thiol group of a Cys residue introduced at at least one of any of the sequence positions that correspond to sequence positions 14, 21, 60, 84, 88, 116, 141, 145, 143, 146 or 158 of the wild type sequence of hNGAL. The moiety that is able to modify the serum half time of said mutein may be selected from the group consisting of a polyalkylene glycol molecule and hydroxyethylstarch.

Where a protein of the invention is a human Lipocalin 2 mutein of the invention, the naturally occurring disulfide bond between Cys 76 and Cys 175 may be removed. Accordingly, such muteins (or any other human Lipocalin 2 mutein that does not include an intramolecular disulfide bond) can be produced in a cell compartment having a reducing redox milieu, for example, in the cytoplasma of Gram-negative bacteria.

In case a lipocalin mutein of the invention includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

However, a mutein of the invention may not necessarily be generated or produced only by use of genetic engineering. Rather, a lipocalin mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for a given target. Methods for the solid phase and/or solution phase synthesis of proteins are well known in the art (reviewed, e.g., in Lloyd-Williams et al. (1997) *Chemical Approaches to the Synthesis of Peptides and Proteins*. CRC Press, Boca Raton, Fields, GB, and Colowick (1997) *Solid-Phase Peptide Synthesis*. Academic Press, San Diego, or Bruckdorfer et al. (2004) *Curr. Pharm. Biotechnol.* 5, 29-43).

In another embodiment, the muteins of the invention may be produced by in vitro transcription/translation employing well-established methods known to those skilled in the art.

The invention also relates to a pharmaceutical composition that includes at least one inventive mutein referred to in the claims or a fusion protein or conjugates thereof and, optionally, a pharmaceutically acceptable excipient.

The lipocalin muteins according to the invention can be administered via any parenteral or non-parenteral (e.g. enteral) route that is therapeutically effective for proteinaceous drugs. Parenteral application methods include, for example, intracutaneous, subcutaneous, intramuscular or intravenous injection and infusion techniques, e.g. in the form of injection solutions, infusion solutions or tinctures, as well as aerosol installation and inhalation, e.g. in the form of aerosol mixtures, sprays or powders. Non-parenteral delivery modes are, for instance, orally, e.g. in the form of pills, tablets, capsules, solutions or suspensions, or rectally, e.g. in the form of suppositories. The muteins of the invention can be administered systemically or topically in formulations containing conventional non-toxic pharmaceutically acceptable excipients or carriers, additives and vehicles as desired.

In one embodiment of the present invention the pharmaceutical is administered parenterally to a vertebrate animal, including a mammal, and in particular to a human. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan and Michniak (2004) *Am. J. Ther.* 11(4), 312-316, can also be used for transdermal delivery of the muteins described herein. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for a chosen ligand as well as on the half-life of the complex between the mutein and the ligand in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of a protein of the invention can be used. However, if wanted, the protein may also be given in a sustained release formulation, for example liposomal dispersions or hydrogel-based polymer microspheres, like PolyActive™ or OctoDEX™ (cf. Bos et al., *Business Briefing: Pharmatech* 2003: 1-6).

Accordingly, the muteins of the present invention can be formulated into compositions using pharmaceutically acceptable ingredients as well as established methods of preparation (Gennaro and Gennaro (2000) *Remington: The Science and Practice of Pharmacy*, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

A mutein of the present invention or a fusion protein or a conjugate thereof can be employed in many applications. In general, such a mutein can be used in all applications antibodies are used, except those which specifically rely on the glycosylation of the Fc part.

A lipocalin mutein described herein can be administered to an organism, including a human patient per se, or in a pharmaceutical composition where it may include or be mixed with pharmaceutically active ingredients or suitable carriers or excipient(s). Techniques for formulation and administration of a respective lipocalin mutein composition resemble or are identical to those of low molecular weight compounds well established in the art. Exemplary routes include, but are not limited to, oral, transdermal, and parenteral delivery. A lipocalin mutein or a respective composition may be used to fill a capsule or tube, or may be provided in compressed form as a pellet. The lipocalin mutein or a respective composition may also be used in injectable or sprayable form, for instance as a suspension of a respective lipocalin mutein.

A composition that includes a lipocalin mutein of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. In some embodiments one may administer a lipocalin mutein or a respective composition in a local rather than systemic manner, for example, via injection.

Pharmaceutical compositions that include a lipocalin mutein of the present invention may be manufactured in a manner that is itself known, e.g., by means of conventional mixing, dissolving, granulating, dragee-making, levigating, emulsifying, encapsulating, entrapping or lyophilizing processes. A pharmaceutical composition for use in accordance with the present invention thus may be formulated in conventional manner using one or more physiologically acceptable carriers including excipients and auxiliaries that facilitate processing of the hydrogel and/or peptide/peptoid into preparations that can be used pharmaceutically. Proper formulation is dependent upon the route of administration chosen.

For injection, the lipocalin mutein or a respective composition may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the lipocalin mutein or a respective composition can be formulated readily by combining them with pharmaceutically acceptable carriers well known in the art. Such carriers enable the lipocalin mutein or a respective composition, as well as a pharmaceutically active compound where present, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides/peptoids may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

A lipocalin mutein of the invention may be formulated for parenteral administration by injection, e.g., by intramuscular injections or bolus injection or continuous infusion. Formulations for injection may be presented in unit dosage form, e.g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

A lipocalin mutein of the invention of the invention may also be used to target a compound to a pre-selected site. In one such embodiment, a lipocalin mutein of the invention is used for the targeting of a pharmaceutically active compound to a pre-selected site in an organism or tissue, comprising:

a) conjugating the lipocalin mutein with said compound, and b) delivering the lipocalin mutein/compound complex to the pre-selected site.

For such a purpose the mutein is contacted with the compound of interest in order to allow complex formation. Then the complex comprising the mutein and the compound of interest are delivered to the pre-selected site. This may, for example, be achieved by coupling the mutein to a targeting moiety, such as an antibody, antibody fragment or lipocalin mutein or lipocalin mutein fragment with binding affinity for the selected target.

This use is in particular suitable, but not restricted to, for delivering a drug (selectively) to a pre-selected site in an organism, such as an infected body part, tissue or organ which is supposed to be treated with the drug. Besides formation of a complex between mutein and compound of interest, the mutein can also be reacted with the given compound to yield a conjugate of mutein and compound. Similar to the above complex, such a conjugate may be suitable to deliver the compound to the pre-selected target site. Such a conjugate of mutein and compound may also include a linker that covalently links mutein and compound to each other. Optionally, such a linker is stable in the bloodstream but is cleavable in a cellular environment.

The muteins disclosed herein and its derivatives can thus be used in many fields similar to antibodies or fragments thereof. In addition to their use for binding to a support, allowing the target of a given mutein or a conjugate or a fusion protein of this target to be immobilized or separated, the muteins can be used for labeling with an enzyme, an antibody, a radioactive substance or any other group having biochemical activity or defined binding characteristics. By doing so, their respective targets or conjugates or fusion proteins thereof can be detected or brought in contact with them. For example, muteins of the invention can serve to detect chemical structures by means of established analytical methods (e.g. ELISA or Western Blot) or by microscopy or immunosensorics. Here, the detection signal can either be generated directly by use of a suitable mutein conjugate or fusion protein or indirectly by immunochemical detection of the bound mutein via an antibody.

Numerous possible applications for the inventive muteins also exist in medicine. In addition to their use in diagnostics and drug delivery, a mutant polypeptide of the invention, which binds, for example, tissue- or tumor-specific cellular surface molecules can be generated. Such a mutein may, for example, be employed in conjugated form or as a fusion protein for "tumor imaging" or directly for cancer therapy.

In a further aspect, the present invention also encompasses the use of a mutein according to the invention for the manufacture of a pharmaceutical composition. The pharmaceutical composition thus obtained may be suited for the treatment of an anaemia. The pharmaceutical composition may be used as monotherapy or as combination therapy. Accordingly, the invention also relates to a mutein as defined above for the treatment of a disease or disorder associated with an altered, e.g. increased or reduced, level of GPC3, such as an anaemia.

In yet another aspect the invention relates to the use of a mutein according to the invention in diagnosis. The use of a mutein according to the invention is typically for the diagnosis of a disease or disorder associated with an altered level of GPC3 as well as a respective method of diagnosis.

Accordingly, the invention also relates to a mutein as defined above for the diagnosis of a disease or disorder associated with an altered, e.g. increased or reduced, level of GPC3. In some embodiments the disease is cancer, including, but not limited to, liver cancer or melanoma. The cancer to be diagnosed is not particularly limited, and specific examples may include liver cancer, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, Wilm's tumor, preferably liver cancer or (primary/early) hepatocellular carcinoma (see Sinnett D. GPC3 (glypican 3). Atlas Genet Cytogenet Oncol Haematol. May 2002).

Also, the invention relates to a method of treating a tumor or cancer, the method comprising administering a pharmaceutical composition as described herein containing a mutein of the invention to a subject in need thereof. Likewise, the invention relates to a mutein of the invention for use in treating a tumor or cancer. Similarly, the invention concerns the use of a mutein of the invention for the preparation of a pharmaceutical composition for treating a tumor or cancer. The cancer or tumor to be treated is not particularly limited, and specific examples may include liver cancer, pancreatic cancer, cholangiocarcinoma, lung cancer, colon cancer, colorectal malignancies, neurofibrosarcoma, neuroblastoma, mammary cancer, breast cancer, ovarian cancer, prostate cancer, leukemia and lymphoma, Wilm's tumor, preferably liver cancer or (primary/early) hepatocellular carcinoma (see Sinnett D. GPC3 (glypican 3). Atlas Genet Cytogenet Oncol Haematol. May 2002).

In still another aspect, the present invention features a diagnostic or analytical kit comprising a mutein according to the present invention.

The subject in need of such a treatment may be a mammal, such as a human, a dog, a mouse, a rat, a pig, an ape such as cynomolgous monkeys to name only a few illustrative examples.

In still another aspect, the present invention features a method for in vivo imaging in a subject, including administering to said subject a mutein of the invention or a pharmaceutical composition comprising a mutein of the invention. The subject may be defined as above.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention is further illustrated by the following non-limiting Examples and the attached drawings. However, these Examples should not be construed so as to limit the invention. Rather, they are merely exemplary embodiments.

Unless otherwise indicated, established methods of recombinant gene technology were used, for example, as described in Sambrook et al. (2001), supra.

Example 1

Construction of a Mutant Lcn2 Phage Display Library

A combinatorial library of Lcn2 variants was generated on the basis of the cloned cDNA (Breustedt et al. (2006) *Biochim. Biophys. Acta* 1764, 161-173), which carried the amino acid substitutions Cys87Ser, to remove the single unpaired thiol side chain (Goetz et al. (2000) *Biochemistry* 39, 1935-1941), as well as Gln28His to introduce a second BstXI restriction site. Mutagenesis and polymerase chain reaction (PCR) assembly of this region was essentially performed according to a published strategy (Beste et al. (1999) *Proc. Natl. Acad. Sci. USA* 96, 1898-1903; Skerra (2001) *J. Biotechnol.* 74, 257-275), this time using a one pot amplification reaction with oligodeoxynucleotides (sequences of SEQ ID NO: 16 to SEQ ID NO: 25) as illustrated in FIG. 1. Oligodeoxynucleotides were designed such that the primers with sequences of SEQ ID NO: 16 to SEQ ID NO: 19 corresponded to the coding strand and carried degenerate codons at the amino acid positions 36, 40, 41, 49, 52, or 68, 70, 72, 73, 77, 79, 81, or 96, 100, 103, 106, or 125, 127, 132, 134 respectively, while primers with sequences of SEQ ID NO: 20 to SEQ ID NO: 23 corresponded to the non-coding strand and did not carry degenerate codons or anticodons. The two flanking primers with SEQ ID NO: 24 and SEQ ID NO: 25 were used in excess and served for the amplification of the assembled randomized gene fragment. All PCR steps were performed using Go-Taq Hot Start DNA polymerase (Promega, Mannheim, Germany) as described (Schlehuber et al. (2000) *J. Mol. Biol.* 297, 1105-1120).

Oligodeoxynucleotides that did not carry degenerate codons were purchased in HPLC grade from Metabion (Munich, Germany). NNK-containing oligodeoxynucleotides were purchased desalted from the same vendor and further purified by urea PAGE. The resulting DNA library was cut with BstXI (Promega, Mannheim, Germany) and cloned on the phagemid vector phNGAL102 (SEQ ID NO: 10), which is based on the generic expression vector pASK111 (Vogt and Skerra (2001) *J. Mol. Recognit.* 14 (1), 79-86) and codes for a fusion protein composed of the OmpA signal peptide, the modified mature Lcn2, followed by an amber codon, and the C-terminal fragment of the gene III coat protein of the filamentous bacteriophage M13, i.e. similar as previously described for the bilin-binding protein (Beste et al., supra; Skerra, supra). After electroporation of *E. coli* XL1-Blue (Bullock et al. (1987) *Biotechniques* 5, 376-378) with the ligation mixture of 8.4 μg digested PCR product and 94 μg digested plasmid DNA, $1 \times 10^{10}$ transformants were obtained.

Alternatively, a cloned synthetic Lcn2 random library, which is described in FIG. 2, was obtained from Sloning BioTechnology GmbH (Puchheim, Germany). The central gene cassette flanked by the two BstXI restriction sites was amplified via PCR in 20 cycles using appropriate primers (SEQ ID NO: 15 and SEQ ID NO: 26) and subcloned on phNGAL108 (SEQ ID NO: 11), which is based on the generic expression vector pASK75 (Skerra (1994) *Gene* 151, 131-135) and carries essentially the same features as phNGAL102 (SEQ ID NO: 10) but mediates ampicillin resistance instead of chloramphenicol resistance and carries a strep-tag I between the mutein and phage pIII protein, in the same way, yielding a library with a complexity corresponding to $1.7 \times 10^{10}$ independent transformants.

The following steps in library generation were performed identically for both Lcn2 libraries. 100 ml of the culture, containing the cells which were transformed with the phasmid vectors on the basis of phNGAL102 or phNGAL108, respectively, coding for the library of the lipocalin muteins as phage pIII fusion proteins, were transferred to a sterile Erlenmeyer flask and incubated for one hour at 37° C., 160 rpm in 2YT medium without antibiotic selection pressure. Before infection with VCS-M13 helper phage the culture was diluted in 2YT medium to an OD550 of 0.1 with the corresponding antibiotic added and further grown under identical conditions until an OD550 of 0.6 was reached. After infection with VCS-M13 helper phage (Agilent Technologies, La Jolla, USA) at a multiplicity of infection of approximately 10 the culture was shaken for additional 30 min at 37° C., 100 rpm. Then the incubator temperature was lowered to 26° C. and the shaker speed was increased again to 160 rpm, after 10 min kanamycin (70 µg/ml) was added, followed by induction of gene expression via addition of anhydrotetracycline (ACROS Organics, Geel, Belgium) at 25 µg/l (125 µl of a 200 µg/ml stock solution in dimethylformamide, DMF per liter of culture). Incubation continued for another 12-15 h at 26° C., 160 rpm.

Cells from the complete culture were sedimented by centrifugation (30 min, 18000 g, 4° C.). The supernatant containing the phagemid particles was sterile-filtered (0.45 µm), mixed with ¼ volume 20% w/v PEG 8000, 15% w/v NaCl, and incubated on ice for at least 2 h. After centrifugation (30 min, 18000 g, 4° C.) the precipitated phagemid particles from 1 liter of culture were dissolved in 30 ml of cold BBS/E (200 mM Na-borate, 160 mM NaCl, 1 mM EDTA pH 8.0) containing 50 mM benzamidine (Sigma) and Pefabloc 1 µg/ml (Roth, Karlsruhe, Germany). The solution was incubated on ice for 1 h. After centrifugation of undissolved components (10 min, 43000 g, 4° C.) each supernatant was transferred to a new reaction vessel.

Addition of ¼ volume 20% w/v PEG 8000, 15% w/v NaCl and incubation for 60 min on ice served to reprecipitate the phagemid particles until the phagemids were aliquoted and frozen at −80° C. for storage. For the first selection cycle phagemids were thawed and centrifuged (30 min, 34000 g, 4° C.), the supernatant was removed, and the precipitated phagemid particles were dissolved and combined in a total of 400 µl PBS containing 50 mM benzamidine. After incubation for 30 min on ice the solution was centrifuged (5 min, 18500 g, 4° C.) in order to remove residual aggregates and the supernatant was used directly for the phage display selection.

Example 2

Procurement of Soluble Recombinant Human Glypican-3

Recombinant human Glypican-3 expressed in NSO cells was purchased from R&D systems and for selection experiments it was randomly biotinylated via Lysine residues using EZ-Link Sulfo-NHS-LC-LC-Biotin (Pierce) at a four-fold molar excess.

Example 3

Phagemid Presentation and Selection of NGAL Muteins with Affinity for Human Glypican-3 (GPC3)

Phagemid display and selection was performed employing the phagemids obtained from Example 1 essentially as described in international patent application WO/2005/019256. The library was subjected to 4 cycles of phage display selection against the recombinant biotinylated human GPC3.

$2 \times 10^{12}$ to $1 \times 10^{13}$ phagemids of the library obtained in Example 1 were used. In brief, the phagemids were centrifuged (21460×g, 4° C., 20 min) and resuspended in 1 ml PBS (4 mM $KH_2PO_4$, 16 mM $Na_2BPO_4$, 115 mM NaCl, pH 7.4) containing 50 mM benzamidine. PBS containing 1% w/v Casein (Sigma) and 0.1% Tween 20® was used as blocking buffer. Prior to the incubation with the target protein, phagemids from the library were incubated either on casein-blocked Neutravidin coated microtiter plates or with casein-blocked Streptavidin beads and Neutravidin for 60 minutes for the depletion of phagemids representing multi-reactive or misfolded lipocalin mutein specific for Neutravidin or Streptavidin bead-specific muteins.

In different Panning approaches a 1 µg/ml solution of target was either captured on Neutavidin-coated (5 µg/ml), 1% Casein-blocked microtiter plates (solid-phase approach) or a 200 nM solution of biotinylated GPC3 was incubated in solution with $1 \cdot 10^{13}$ phagemids from the NGAL library blocked with 1% Casein (solution approach). In the solution approach target bound phagemids were captured via Streptavidin™-coated magnetic beads (Invitrogen/Dynal) or Neutravidin-coated magnetic beads (Distrilab) in alternating manner within 20 min, followed by 8 wash cycles and elution with either 300 µL 70 mM Triethylamin for 10 min, and neutralization with an appropriate amount of 1 M Tris/HCl, pH 7.4 (basic elution) followed by 300 µL 0.1 M Glycin/HCl pH 2.2 for 10 min. and neutralization with an appropriate amount of 0.5 M Tris-Base (acidic elution) or with bacterial elution.

In the solid-phase approach blocked phagemids were incubated with the biotinylated target followed by 8 wash cycles and elution as described above. Beginning with the second enrichment cycle, only half of the combined phagemid solutions were used for phagemid amplification.

Phagemid amplification between each panning cycle was performed as described in Schlehuber, S. et al. (*J. Mol. Biol.* (2000), 297, 1105-1120).

Three further selection rounds against Glypican-3 were carried out in this way employing the preparation of amplified phagemids from the respective previous enrichment cycle with the exception that only about $1 \times 10^{11}$ phagemids were utilized beginning with the second enrichment cycle.

Example 4

Identification of hGPC-3-Specific Muteins Using High-Throughput ELISA Screening

Screening of the muteins selected according to Example 3 was performed essentially as described in Example 3 of international patent application WO 2006/56464.

Lipocalin muteins from round three and four of the previously described panning process were selected in a HT-screening ELISA. Therein, NGAL variants equipped with a T7 detection tag (Novagen) as well as a Strep-tag II affinity tag (IBA) were soluble expressed in a 96 well microtiter plate using the *E. coli* strain TG1/F⁻ with phNGAL 101. This vector corresponds to phNGAL 98 (SEQ ID NO: 9) with an N-terminal T7 tag consisting of 11 amino acids (MASMTGGQQMG) (residues 187-197 of SEQ ID NO: 12, see also FIG. 4B). Lipocalin mutein expression was induced overnight at 22° C. at 700 rpm with anhydrotetracycline (0.2 µg/ml) at an $OD_{550}$ of 0.6. Afterwards, cells were lysed (100 mM Na-borate, pH 8.0, 80 mM NaCl, 1 mM EDTA, 0.025% w/v lysozyme) for 1 h under agitation. To minimize non-specific binding in the subsequent ELISA screen, the crude cell lysates were supplemented with 2% w/v BSA and 0.1% v/v Tween 20 and tested in ELISA for binding to human Glypican-3. Therefore, biotinylated human GPC-3 was captured with 1 µg/ml via immobilized Neutravidin (5 µg/ml, Thermo Scientific) on wells of black Fluotrac 600 ELISA plates (Greiner; 384 well). Neutravidin, Streptavidin, 5 µg/ml each, and 3% milk were used as negative control. Plates were blocked with PBST/0.1 containing 2% w/v BSA, and subsequently incubated with the bacterial cell extract for 1 h at room temperature plates were washed five times and bound Lipocalin muteins were detected via an anti-T7 monoclonal antibody-HRP conjugate (Novagen), diluted 1:10.000 in PBST/0.1. Therefore, QuantaBlu™ (Pierce; 1:2 diluted in PBS/T 0.1%) was used as fluorogenic HRP substrate. After 45 min of signal development at room temperature fluorescence was excited at a wavelength of 320 nm (±12.5 nm) and measured at 430 nm (±17.5 nm) in a GENiosPlus plate reader (Tecan).

In a reverse ELISA approach soluble expressed muteins from the crude cell lysate were captured in ELISA plates via a rabbit polyclonal NGAL-specific antibody following incubation with varying amounts of biotinylated human Glypican-3 (10, 5, and 1 nM) to reach target-limiting conditions in order to differentiate the muteins by their affinity. Binding of the target was detected via Neutravidin-HRP conjugate (Pierce). One could compete for mutein binding by the addition of 100 nM non-biotinylated human Glypican-3 indicating, that the muteins bind the non-modified human Glypican-3 as well. The identical assay approach was also used to compete with 100 nM of non-modified Glypican-5 (R&D Systems) in order to demonstrate target specificity.

Screening of 1440 clones, selected as described in Example 3, led to the identification of more then 700 primary hits indicating the successful isolation of target-specific muteins. The reverse ELISA approach under target-limiting conditions and the competition ELISA allowed for a differentiation of GPC3-specific muteins in terms of their target affinity and specificity. Using these ELISA approaches the clones with SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, were identified. The sequences of these muteins are depicted in FIG. 3.

Example 5

Production of Glypican3-Binding Muteins (NGAL)

The recombinant Lcn2 and the human Glypican-3-specific Lcn2 variants were produced by periplasmic secretion in *E. coli* $K_{12}$ strain JM83 (Yanisch-Perron et al. (1985) Gene 33, 103-119), the *E. coli* supE strain TG1-F- (a derivative of *E. coli* K12 TG1 [Kim et al. (2009) J. Am. Chem. Soc. 131, 3565-3576] that was cured from its episome using acridinium orange), or *E. coli* W3110 (Bachmann (1990) Microbiol. Rev. 54, 130-197).

For a small scale soluble protein expression the plasmid phNGAL98 (SEQ ID NO: 9) was used, encoding a fusion of the OmpA signal peptide with the respective mutein and the C-terminal Strep-tag II, whereby the plasmid carries the two non-compatible BstXI restriction sites for unidirectional subcloning of the mutated gene cassette. Growth was allowed to occur in a 2 L shaking flask culture in the presence of LB-Ampicillin medium according to the protocol described in Schlehuber, S. et al. (*J. Mol. Biol.* (2000), 297, 1105-1120). For larger amounts of protein the periplasmatic production was performed with the same vector expressed in the *E. coli* strain W3110 via bench top fermenter cultivation in a 1 l or 10 l vessel based on the protocol described in Schiweck, W., and Skerra, A. *Proteins* (1995) 23, 561-565).

The Lcn2 variants were purified from the periplasmic fraction in a single step via streptavidin affinity chromatography (Strep-Tactin™ Superflow, IBA) using a column of appropriate bed volume according to the procedure described by Skerra, A. & Schmidt, T. G. M. (2000) (Use of the Strep-tag and streptavidin for detection and purification of recombinant proteins. *Methods Enzymol*. 326A, 271-304). To achieve higher purity and to remove any aggregated recombinant protein, a gel filtration of the muteins was finally carried out on a Superdex 75 HR 10/30 column (24-ml bed volume, Amersham Pharmacia Biotech, Freiburg, Germany) in the presence of PBS buffer. The monomeric protein fractions were pooled, analysed for purity by SDS-PAGE (Fling and Gregerson (1986) *Anal. Biochem.* 155, 83-88), and used for further biochemical characterization.

Example 6

Affinity Measurement Using ELISA Techniques

A "direct" ELISA was performed to verify the binding affinity and specificity of the selected Lcn2 muteins. Therefore, a constant concentration of 1 µg/ml biotinylated human Glypican 3 (R&D Systems) was captured on the surface of a polystyrol plate (Greiner, GE) via BSA blocked Neutravidin (Thermo Scientific, 5 µg/ml). Two step dilution series of purified Lcn2 muteins were incubated with the captured GPC-3 for 1 h at room temperature and detected either via the Strep-tag II using a rabbit anti-strep-tag II polyconal antibody (GenScript, USA) or by using a scaffold-specific polyclonal rabbit antibody. In both cases an anti rabbit IgG-HRP conjugate (Abcam, UK) was employed as secondary detection antibody.

The absorption ΔA at 320 nm was measured in an ELISA reader (Tecan, GE) and the data were fitted with Graphpad Prism software (Statcom, USA).

Results from measurements employing the muteins of the sequences of SEQ ID NO: 1 to SEQ ID NO: 8, as well as of SEQ ID NO: 9 as a negative control are summarized in Table 1.

TABLE 1

Affinity constants of muteins to the target human Glypican-3

| Mutein | KD [nM] |
|---|---|
| PIE-G3A | 7.6 |
| PIE-G3B | 0.27 |
| PIE-G3C | 0.32 |

TABLE 1-continued

Affinity constants of muteins to the target human Glypican-3

| Mutein | KD [nM] |
|---|---|
| PIE-G3D | 0.46 |
| PIE-G3E | 0.2 |
| PIE-G3F | 0.35 |
| PIE-G3G | 0.27 |
| PIE-G3H | 0.3 |

Figure 4:
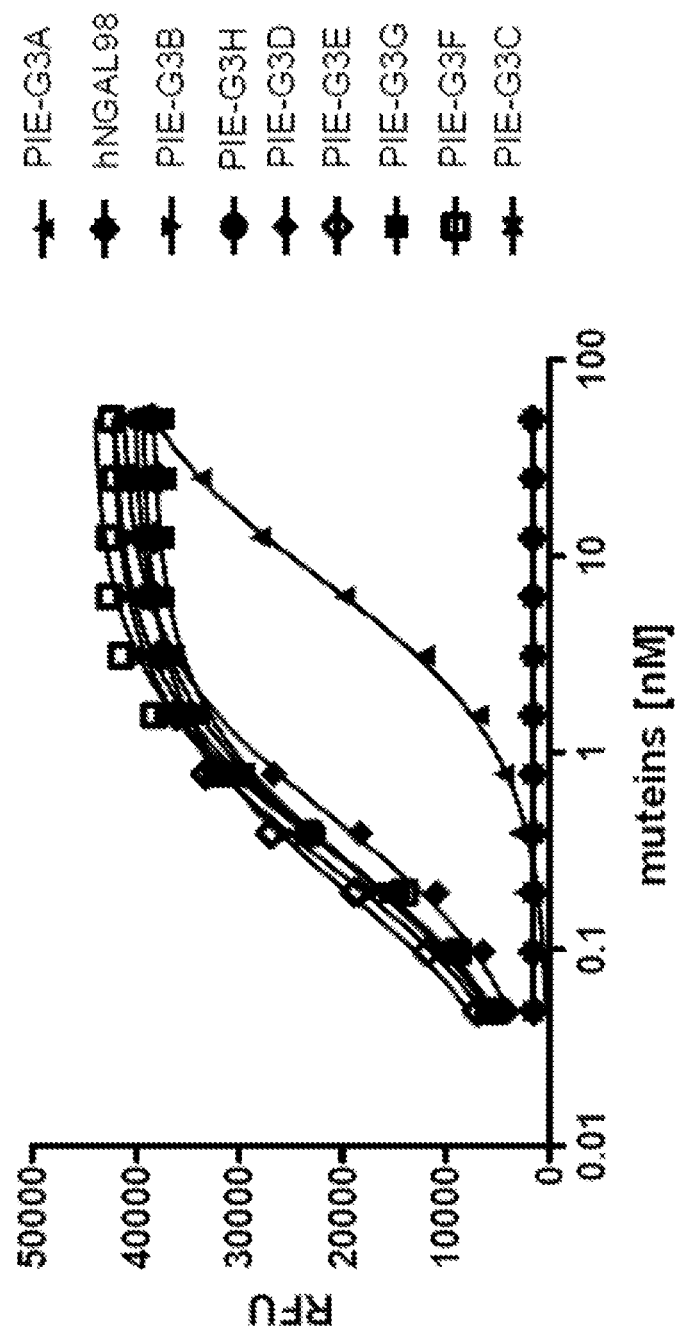
FIG. 4 shows the graphical representation of a direct ELISA of selected Lcn2 muteins for human Glypican-3. Lcn2 wildtype protein revealed negligible signals in this assay for Glypican-3, which served as a negative control.

$K_D$ values of the selected Lcn2 muteins vary from 200 µM up to 7.6 nM, whereas the negative control showed no binding at all. FIG. 4 shows a graphical representation of these data.

The binding affinity of the Lcn2 muteins to non-modified Glypican-3 in solution was evaluated in a competition ELISA approach. Therefore, a constant concentration of 1 µg/ml biotinylated human Glypican-3 (R&D Systems) was captured on the surface of a polystyrol plate (Greiner, GE) via Neutravidin (Thermo Scientific, 5 µg/ml, GE). In parallel a two step dilution series of non-biotinylated human Glypican-3 starting from 1.5 µM was incubated with a constant concentration of GPC3-specific mutein for 1 h at room temperature in a non-protein binding 96 well polypropylene plate (Nunc, GE). The constant concentration of lipocalin muteins corresponds to the $EC_{50}$ of the respective muteins as determined in a direct ELISA as described above in this example. In the following the mixture of non-modified human GPC3 and lipocalin mutein was transferred onto the GPC3-captured Neutravidin plate. The biotinylated GPC3 was allowed to compete with the non-modified GPC3 for Anticalin binding for 1 h at room temperature. During these 1 h, free lipcocalin mutein was bound to the captured GPC3 and detected via a rabbit anti-strep-tag II polyconal antibody (GenScript, USA). A goat anti-rabbit IgG-HRP conjugate (Abcam, UK) was employed as secondary detection antibody. Parallel to the competition assay, anticalin binding was determined on the same plate in a "direct" ELISA, in order to obtain a standard curve linking the RFU values to anticalin concentration. This curve was then used to standardize competition data to the level of anticalins bounds to the plate and fitted with Graphpad software. $IC_{50}$ values correspond to the half-maximum amount of lipocalin mutein bound to the plate.

Results from measurements employing the muteins of the sequences of SEQ ID NO: 1 to SEQ ID NO: 8 are summarized in FIG. 5.

$IC_{50}$ values of the selected Lcn2 muteins vary from 70 pM up to 1 nM.

Example 7

Measurement of Binding Affinity for Glypican-3 Via Surface Plasmon Resonance on a Biacore T100 Instrument Surface plasmon resonance was used to measure binding kinetics and affinity of the lipocalin muteins disclosed herein. Real time analysis of the binding of the Lcn2 muteins to Glypican-3 was performed on a Biacore T100 system (GE Healthcare Bio-Sciences AB, Uppsala, Sweden) using HBS-EP+ (BR-1006-69, GE Healthcare Bio-Sciences AB, Uppsala, Sweden) as running buffer. A 10 µg/mL solution of Glypican-3 in 10 mM sodium acetate pH 4.5 was immobilized onto a CM5 chip (GE Healthcare Bio-Sciences AB, Uppsala, Sweden) using standard amine coupling chemistry, resulting in a ligand density of 467 RU. The purified Lcn2 muteins were applied in concentrations of 40 nM and 120 nM at a flow rate of 30 µL/min. The dilutions were injected with association times of 120 sec and dissociation times of 420 sec to obtain ka and kd information. Regeneration of the ligand was achieved by injecting either 6 M Guanidinium-HCl (120 sec/300 sec) or 3 M MgCl2 (900 sec) with a flow rate of 10 µL/min. Injection of regeneration solutions was followed by an extra wash step with running buffer and a stabilization period of 180 sec.

The data were double-referenced by subtraction of the corresponding signals measured for the control channel, which had been activated and blocked with ethanolamine and by substraction of buffer injections from the binding responses. ka and kd for the binding reaction were determined using Biacore T100 Evaluation Software V2.0.1 for data processing and kinetic fitting. The data were globally fit with 1:1 binding model.

The values determined for ka and kd for the muteins of the sequences of SEQ ID NO: 1 to SEQ ID NO: 8 are summarized in FIG. 6.

Example 8

Species-Crossreactivity of Glypican 3 Muteins on SK-Hep1 Transfectants

SK-HEP1 from the DSMZ cell bank which do not express detectable levels of endogenous GPC3 as assessed by flow cytometry were stably transfected with an expression vector encoding human, cynomolgus or mouse GPC3. Empty vector control cells were also obtained and analyzed in parallel. Detection of GPC3 was achieved using mouse anti-glypican 3 clone 1G12 monoclonal antibody (DCS).

In order to assess binding of muteins to the GPC3 on the cell surface, 200,000 cells in PBS/2% FCS were used in each binding reaction. Reactions were performed on ice in 30 µl for 2 h. Following two washing steps in PBS/2% FCS a secondary rabbit anti-hNGAL scaffold antiserum was employed for 30 min. followed another two wash steps. Detection was achieved with anti-rabbit IgG-PE (30 min.). Measurements were performed on a FACSCalibur flow cytometer where 10,000 events were acquired for each sample. Geometric mean values were compiled in FlowJo (Treestar software) and fitted to a sigmoidal dose response model in the Prism 5 program (GraphPad) to obtain EC50 values.

FIG. 7 shows binding affinities to human, cyno, and mouse GPC3 transfected SK-Hep1 cells.

The invention claimed is:

1. A mutein of human Lipocalin 2 (hNGAL) comprising amino acid substitutions at nine or more of any of the sequence positions corresponding to sequence positions 36, 40, 41, 49, 52, 68, 70, 72, 73, 77, 79, 81, 96, 100, 103, 106, 125, 127, 132, and 134 of the linear polypeptide sequence of hNGAL (SEQ ID NO: 27), wherein the mutein is capable of binding glypican-3 (GPC3) with an affinity by a $K_D$ of about 10 nM or lower.

2. The mutein of claim 1, wherein the mutein comprises, with respect to the linear polypeptide sequence of hNGAL, one or more amino acid substitutions selected from the group consisting of: Leu 36→Ile, Val, Arg, Met or Ser; Ala 40→Trp, Val, His, Gly or Tyr; Ile 41→Met, Ala, Arg, Gln or Ser; Gln 49→Pro, Leu, Val, Arg or Trp; Tyr 52→Arg, Thr, His, Ser or Asn; Ser 68→Arg, Gly, Asn, Ala or Lys; Leu 70→Arg, Ser, Gln, Thr or Phe; Arg 72→Asp, Trp, Ala or Ser; Lys 73→Glu, Arg, Met, Leu or His; Asp 77→Gly, His, Met, Gln, Ser or Tyr; Trp 79→Gly, Lys, Ser or Ile; Arg 81→Ala, Gly, Thr, Tyr or Trp; Asn 96→Val, Asp, Gln, Lys, Gly or Phe; Tyr 100→Arg, Gly, Glu, Ile or Asn; Leu 103→Ile, Gln, Asn, Met, Asp or Trp; Tyr 106→Asp, Asn, Met, Phe or Leu; Lys 125→Phe, Glu, Arg, Tyr, Gly or Trp; Ser 127→Lys, Arg, Tyr, His, Ile or Asp; Tyr 132→Trp, Ile, Phe, Gln or Val; and Lys 134→Gly, Ala, Phe, Asp, Asn, Ile or Ser.

3. The mutein of claim 1, wherein the amino acid sequence of the mutein comprises, with respect to the linear polypeptide sequence of hNGAL, one set of the amino acid substitutions selected from the group consisting of:

(a) Leu 36→Ile; Ala 40→Trp; Gln 49→Pro; Tyr 52→Arg; Ser 68→Arg; Leu 70→Arg; Arg 72→Asp; Lys 73→Glu; Asp 77→Gly; Trp 79→Gly; Arg 81→Ala; Asn 96→Val; Tyr 100→Arg; Leu 103→Ile; Tyr 106→Asp; Lys 125→Phe; Ser 127→Lys; Lys 134→Gly;

(b) Leu 36→Val; Ile 41→Met; Gln 49→Leu; Tyr 52→Arg; Ser 68→Gly; Leu 70→Ser; Arg 72→Trp; Lys 73→Arg; Asp 77→His; Trp 79→Lys; Arg 81→Gly; Asn 96→Asp; Tyr 100→Gly; Leu 103→Gln; Tyr 106→Asn; Lys 125→Glu; Ser 127→Arg; Tyr 132→Trp; Lys 134→Ala;

(c) Leu 36→Arg; Ala 40→Val; Ile 41→Ala; Gln 49→Pro; Tyr 52→Arg; Ser 68→Asn; Leu 70→Arg; Arg 72→Ala; Lys 73→Met; Asp 77→Met; Trp 79→Ser; Arg 81→Gly; Asn 96→Gln; Tyr 100→Glu; Leu 103→Asn; Tyr 106→Asn; Lys 125→Glu; Ser 127→Tyr; Tyr 132→Ile; Lys 134→Phe;

(d) Leu 36→Met; Ile 41→Arg; Gln 49→Val; Tyr 52→Thr; Ser 68→Ala; Leu 70→Gln; Lys 73→Leu; Asp 77→Gln; Trp 79→Gly; Arg 81→Thr; Asn 96→Asp; Tyr 100→Ile; Tyr 106→Met; Lys 125→Arg; Ser 127→Arg; Tyr 132→Phe; Lys 134→Asp;

(e) Leu 36→Ser; Ala 40→His; Ile 41→Arg; Gln 49→Arg; Tyr 52→His; Ser 68→Asn; Leu 70→Thr; Lys 73→Glu; Asp 77→His; Trp 79→Ser; Arg 81→Gly; Asn 96→Lys; Tyr 100→Asn; Leu 103→Met; Tyr 106→Phe; Ser 127→His; Tyr 132→Gln; Lys 134→Asn;

(f) Leu 36→Ile; Ala 40→Gly; Ile 41→Gln; Gln 49→Trp; Tyr 52→Ser; Leu 70→Arg; Lys 73→Leu; Asp 77→Ser; Arg 81→Tyr; Asn 96→Gly; Tyr 100→Asn; Leu 103→Asp; Tyr 106→Asn; Lys 125→Tyr; Ser 127→Ile; Tyr 132→Trp; Lys 134→Ile;

(g) Leu 36→Met; Ile 41→Ser; Gln 49→Arg; Tyr 52→Asn; Ser 68→Lys; Leu 70→Arg; Arg 72→Trp; Lys 73→His;

Asp 77→Tyr; Trp 79→Ser; Arg 81→Thr; Asn 96→Asp; Leu 103→Trp; Lys 125→Gly; Ser 127→Arg; Tyr 132→Trp; Lys 134→Ser;

(h) Leu 36→Ile; Ala 40→Tyr; Gln 49→Pro; Tyr 52→Arg; Ser 68→Arg; Leu 70→Phe; Arg 72→Ser; Lys 73→Arg; Trp 79→Ile; Arg 81→Trp; Asn 96→Phe; Tyr 100→Asn; Tyr 106→Leu; Lys 125→Trp; Ser 127→Asp; Tyr 132→Val; Lys 134→Gly.

4. The mutein of claim 1, wherein the mutein competes for binding to GPC3 with an $IC_{50}$ value of about 1 nM or lower in an ELISA competition assay.

5. The mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

6. The mutein of claim 1, wherein the mutein is fused at its N-terminus and/or its C-terminus to a fusion partner which is a protein, a protein domain, or a peptide.

7. The mutein of claim 1, wherein the mutein is conjugated to a compound that extends the serum half-life of the mutein.

8. The mutein of claim 7, wherein the compound that extends the serum half-life is selected from the group consisting of a polyalkylene glycol molecule, hydroethylstarch, an Fc part of an immunoglubolin, a CH3 domain of an immoglobulin, a CH4 domain of an immunoglubolin, an albumin binding peptide, and an albumin binding protein.

9. A nucleic acid molecule comprising a nucleotide sequence encoding the mutein of claim 1.

10. The nucleic acid molecule of claim 9, wherein the nucleic acid molecule is operably linked to a regulatory sequence to allow expression of said nucleic acid molecule.

11. The nucleic acid molecule of claim 9, wherein the nucleic acid molecule is comprised in a vector or in a phagemid vector.

12. An isolated host cell containing the nucleic acid molecule of claim 9.

13. A method of producing the mutein of claim 1 or a fusion protein of the mutein and another polypeptide, wherein the mutein or the fusion protein is produced by subjecting a nucleic acid encoding hNGAL to mutagenesis at nine or more of any of the encoded amino acid sequence positions corresponding to sequence positions 36, 40, 41, 49, 52, 68, 70, 72, 73 77, 79, 81, 96, 100, 103, 106, 125, 125, 127, 132, and 134 of the linear polypeptide sequence of hNGAL (SEQ ID NO: 27).

14. The method of claim 13, wherein the mutein or the fusion protein is produced in an isolated bacterial or eukaryotic host organism and then isolated from the host organism or its culture.

15. A pharmaceutical composition comprising the mutein of claim 1 and a pharmaceutically acceptable excipient.

16. A kit for detecting the presence of GPC3 comprising the mutein of claim 1.

17. A method of detecting the presence of GPC3, comprising the steps of:

(a) contacting the mutein of claim 1 with a test sample suspected to contain GPC3, thereby allowing the formation of a complex between the mutein and GPC3, and (b) detecting the complex between the mutein and GPC3 by a suitable signal.

18. A mutein of hNGAL comprising an amino acid sequence selected from the group consisting of SEQ ID NOs: 1-8.

* * * * *

SEQUENCE LISTING

<160> NUMBER OF SEQ ID NOS: 52

<210> SEQ ID NO 1
<211> LENGTH: 188
<212> TYPE: PRT
<213> ORGANISM: Artificial Sequence

```
<220> FEATURE:
<223> OTHER INFORMATION: Description of Artificial Sequence: Synthetic
      Mutein of hNGAL (G08) polypeptide

<400> SEQUENCE: 1

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Ile Ala Gly Asn Trp Ile Leu Arg Glu Lys Asp Pro
            35                  40                  45

Pro Lys Met Arg Ala Thr Ile Tyr Glu Leu Lys Glu Asp Lys Ser Tyr
50                  55                  60

Asn Val Thr Arg Val Arg Phe Asp Glu Lys Lys Cys Gly Tyr Gly Ile
65                  70                  75                  80

Ala Thr Phe Val Pro Gly Ser Gln Pro Gly Glu Phe Thr Leu Gly Val
                85                  90                  95

Ile Lys Ser Arg Pro Gly Ile Thr Ser Asp Leu Val Arg Val Val Ser
                100                 105                 110

Thr Asn Tyr Asn Gln His Ala Met Val Phe Phe Lys Phe Val Lys Gln
            115                 120                 125

Asn Arg Glu Tyr Phe Gly Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 2
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (A16) polypeptide

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Val Ala Gly Asn Ala Met Leu Arg Glu Asp Lys Asp Pro
            35                  40                  45

Leu Lys Met Arg Ala Thr Ile Tyr Glu Leu Lys Glu Asp Lys Ser Tyr
    50                  55                  60

Asn Val Thr Gly Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
                100                 105                 110

Thr Asn Tyr Asn Gln His Ala Met Val Phe Phe Lys Glu Val Arg Gln
            115                 120                 125

Asn Arg Glu Trp Phe Ala Ile Thr Leu Tyr Gly Arg Thr Lys Glu Leu
            130                 135                 140
```

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 3
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (M02) polypeptide

<400> SEQUENCE: 3

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Arg Ala Gly Asn Val Ala Leu Arg Glu Asp Lys Asp Pro
            35                  40                  45

Pro Lys Met Arg Ala Thr Ile Tyr Glu Leu Lys Glu Asp Lys Ser Tyr
50                  55                  60

Asn Val Thr Asn Val Arg Phe Ala Met Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
                100                 105                 110

Thr Asn Tyr Asn Gln His Ala Met Val Phe Phe Lys Lys Val Tyr Gln
                115                 120                 125

Asn Arg Glu Ile Phe Phe Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 4
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (K21) polypeptide

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Met Ala Gly Asn Ala Arg Leu Arg Glu Asp Lys Asp Pro
            35                  40                  45

Val Lys Met Thr Ala Thr Ile Tyr Glu Leu Lys Glu Asp Lys Ser Tyr
50                  55                  60
```

```
Asn Val Thr Ala Val Gln Phe Arg Leu Lys Lys Cys Gln Tyr Gly Ile
 65                  70                  75                  80

Thr Thr Phe Val Pro Gly Ser Gln Pro Gly Glu Phe Thr Leu Gly Asp
                 85                  90                  95

Ile Lys Ser Ile Pro Gly Leu Thr Ser Met Leu Val Arg Val Val Ser
                100                 105                 110

Thr Asn Tyr Asn Gln His Ala Met Val Phe Phe Lys Arg Val Arg Gln
            115                 120                 125

Asn Arg Glu Phe Phe Asp Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 5
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (024) polypeptide

<400> SEQUENCE: 5

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                20                  25                  30

Val Val Gly Ser Ala Gly Asn His Arg Leu Arg Glu Asp Lys Asp Pro
            35                  40                  45

Arg Lys Met His Ala Thr Ile Tyr Glu Leu Lys Glu Asp Lys Ser Tyr
 50                  55                  60

Asn Val Thr Asn Val Thr Phe Arg Glu Lys Lys Cys His Tyr Ser Ile
 65                  70                  75                  80

Gly Thr Phe Val Pro Gly Ser Gln Pro Gly Glu Phe Thr Leu Gly Lys
                 85                  90                  95

Ile Lys Ser Asn Pro Gly Met Thr Ser Phe Leu Val Arg Val Val Ser
                100                 105                 110

Thr Asn Tyr Asn Gln His Ala Met Val Phe Phe Lys Lys Val His Gln
            115                 120                 125

Asn Arg Glu Gln Phe Asn Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 6
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (002) polypeptide -continued

```
<400> SEQUENCE: 6

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Gly Gln Leu Arg Glu Asp Lys Asp Pro
        35                  40                  45

Trp Lys Met Ser Ala Thr Ile Tyr Glu Leu Lys Glu Asp Lys Ser Tyr
    50                  55                  60

Asn Val Thr Ser Val Arg Phe Arg Leu Lys Lys Cys Ser Tyr Trp Ile
65                  70                  75                  80

Tyr Thr Phe Val Pro Gly Ser Gln Pro Gly Glu Phe Thr Leu Gly Gly
                85                  90                  95

Ile Lys Ser Asn Pro Gly Asp Thr Ser Asn Leu Val Arg Val Val Ser
            100                 105                 110

Thr Asn Tyr Asn Gln His Ala Met Val Phe Phe Lys Tyr Val Ile Gln
        115                 120                 125

Asn Arg Glu Trp Phe Ile Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 7
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (M04) polypeptide

<400> SEQUENCE: 7

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Ala Ser Leu Arg Glu Asp Lys Asp Pro
        35                  40                  45

Arg Lys Met Asn Ala Thr Ile Tyr Glu Leu Lys Glu Asp Lys Ser Tyr
    50                  55                  60

Asn Val Thr Lys Val Arg Phe Trp His Lys Lys Cys Tyr Tyr Ser Ile
65                  70                  75                  80

Thr Thr Phe Val Pro Gly Ser Gln Pro Gly Glu Phe Thr Leu Gly Asp
                85                  90                  95

Ile Lys Ser Tyr Pro Gly Trp Thr Ser Tyr Leu Val Arg Val Val Ser
            100                 105                 110

Thr Asn Tyr Asn Gln His Ala Met Val Phe Phe Lys Gly Val Arg Gln
        115                 120                 125

Asn Arg Glu Trp Phe Ser Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160
```

Leu Pro Glu Asn His Ile Val Phe Pro Val Pro Ile Asp Gln Cys Ile
            165                 170                 175

Asp Gly Ser Ala Trp Ser His Pro Gln Phe Glu Lys
            180                 185

<210> SEQ ID NO 8
<211> LENGTH: 188
<212> TYPE: PRT
<213> ORGANISM: Artificial Sequence
<220> FEATURE:
<223> OTHER INFORMATION: Description of Artificial Sequence: Synthetic
      Mutein of hNGAL (O12) polypeptide

<400> SEQUENCE: 8

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Tyr Ile Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Arg Val Phe Phe Ser Arg Lys Lys Cys Asp Tyr Ile Ile
65                  70                  75                  80

Trp Thr Phe Val Pro Gly Ser Gln Pro Gly Glu Phe Thr Leu Gly Phe
                85                  90                  95

Ile Lys Ser Asn Pro Gly Leu Thr Ser Leu Leu Val Arg Val Val Ser
            100                 105                 110

Thr Asn Tyr Asn Gln His Ala Met Val Phe Phe Lys Trp Val Asp Gln
        115                 120                 125

Asn Arg Glu Val Phe Gly Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 9
<211> LENGTH: 3745
<212> TYPE: DNA
<213> ORGANISM: Artificial Sequence
<220> FEATURE:
<223> OTHER INFORMATION: Description of Artificial Sequence: Synthetic
      Expression vector phNGAL98 with AmpR encoding
      wild type Lcn2 with the C-terminal Strep-tagII

<400> SEQUENCE: 9
ccatcgaatg gccagatgat taattcctaa ttttttgttga cactctatca ttgatagagt     60
tattttacca ctccctatca gtgatagaga aaagtgaaat gaatagttcg acaaaaatct    120
agataacgag ggcaaaaaat gaaaagaca gctatcgcga ttgcagtggc tctggctggc    180
ttcgctaccg tagcgcaggc ccaggactcc acctcagacc tgatcccagc cccacctctg    240
agcaaggtcc ctctgcagca gaacttccag gacaaccaat tccatgggaa gtggtatgtg    300
gtaggtctcg cagggaatgc aattctcaga agagacaaag acccgcaaaa gatgtatgcc    360
accatctatg agctgaaaga agacaagagc tacaatgtca cctccgtcct gtttaggaaa    420

```
aagaagtgtg actactggat caggactttt gttccaggtt cccagccagg cgagttcacg    480
ctgggcaaca ttaagagtta ccctggatta acgagttacc tcgtccgagt ggtgagcacc    540
aactacaacc agcatgctat ggtgttcttc aagaaagttt ctcaaaacag ggagtacttc    600
aagatcaccc tctacgggag aaccaaggag ctgacttcgg aactaaagga gaacttcatc    660
cgcttctcca aatctctggg cctccctgaa aaccacatcg tcttccctgt cccaatcgac    720
cagtgtatcg acggcagcgc ttggtctcac ccgcagttcg aaaaataata agcttgacct    780
gtgaagtgaa aaatggcgca cattgtgcga cattttttt gtctgccgtt taccgctact     840
gcgtcacgga tctccacgcg ccctgtagcg gcgcattaag cgcggcgggt gtggtggtta    900
cgcgcagcgt gaccgctaca cttgccagcg ccctagcgcc cgctcctttc gctttcttcc    960
cttcctttct cgccacgttc gccggctttc ccgtcaagc tctaaatcgg gggctccctt     1020
tagggttccg atttagtgct ttacggcacc tcgaccccaa aaaacttgat tagggtgatg   1080
gttcacgtag tgggccatcg ccctgataga cggtttttcg ccctttgacg ttggagtcca    1140
cgttctttaa tagtggactc ttgttccaaa ctggaacaac actcaaccct atctcggtct    1200
attcttttga tttataaggg attttgccga tttcggccta ttggttaaaa aatgagctga   1260
tttaacaaaa atttaacgcg aatttttaaca aaatattaac gttacaatt tcaggtggca    1320
cttttcgggg aaatgtgcgc ggaacccta tttgtttatt tttctaaata cattcaaata    1380
tgtatccgct catgagacaa taaccctgat aaatgcttca ataatattga aaaggaaga    1440
gtatgagtat tcaacatttc cgtgtcgccc ttattccctt ttttgcggca ttttgccttc    1500
ctgttttgc tcacccagaa acgctggtga agtaaaaga tgctgaagat cagttgggtg    1560
cacgagtggg ttacatcgaa ctggatctca acagcggtaa gatccttgag agttttcgcc    1620
ccgaagaacg ttttccaatg atgagcactt ttaaagttct gctatgtggc gcggtattat    1680
cccgtattga cgccgggcaa gagcaactcg gtcgccgcat acactattct cagaatgact   1740
tggttgagta ctcaccagtc acagaaaagc atcttacgga tggcatgaca gtaagagaat    1800
tatgcagtgc tgccataacc atgagtgata acactgcggc caacttactt ctgacaacga    1860
tcggaggacc gaaggagcta accgcttttt tgcacaacat gggggatcat gtaactcgcc   1920
ttgatcgttg ggaaccggag ctgaatgaag ccataccaaa cgacgagcgt gacaccacga    1980
tgcctgtagc aatggcaaca acgttgcgca aactattaac tggcgaacta cttactctag   2040
cttcccggca caattgata gactggatgg aggcggataa agttgcagga ccacttctgc    2100
gctcggccct tccggctggc tggtttattg ctgataaatc tggagccggt gagcgtggct    2160
ctcgcggtat cattgcagca ctggggccag atggtaagcc ctcccgtatc gtagttatct    2220
acacgacggg gagtcaggca actatggatg aacgaaatag acagatcgct gagataggtg    2280
cctcactgat taagcattgg taggaattaa tgatgtctcg tttagataaa agtaaagtga    2340
ttaacagcgc attagagctg cttaatgagg tcggaatcga aggtttaaca acccgtaaac    2400
tcgcccagaa gctaggtgta gagcagccta cattgtattg gcatgtaaaa aataagcggg    2460
ctttgctcga cgccttagcc attgagatgt tagataggca ccatactcac ttttgccctt    2520
tagaagggga aagctggcaa gatttttac gtaataacgc taaaagtttt agatgtgctt    2580
tactaagtca tcgcgatgga gcaaaagtac atttaggtac acggcctaca gaaaaacagt    2640
atgaaactct cgaaaatcaa ttagcctttt tatgccaaca aggttttca ctagagaatg    2700
cattatatgc actcagcgca gtggggcatt ttactttagg ttgcgtattg gaagatcaag    2760
agcatcaagt cgctaaagaa gaaagggaaa cacctactac tgatagtatg ccgccattat    2820
```

```
tacgacaagc tatcgaatta tttgatcacc aaggtgcaga gccagccttc ttattcggcc      2880
ttgaattgat catatgcgga ttagaaaaac aacttaaatg tgaaagtggg tcttaaaagc      2940
agcataacct ttttccgtga tggtaacttc actagtttaa aaggatctag gtgaagatcc      3000
tttttgataa tctcatgacc aaaatcccct taacgtgagt ttcgttccac tgagcgtcag      3060
accccgtaga aaagatcaaa ggatcttctt gagatccttt ttttctgcgc gtaatctgct      3120
gcttgcaaac aaaaaaacca ccgctaccag cggtggtttg tttgccggat caagagctac      3180
caactctttt tccgaaggta actggcttca gcagagcgca gataccaaat actgtccttc      3240
tagtgtagcc gtagttaggc caccacttca agaactctgt agcaccgcct acatacctcg      3300
ctctgctaat cctgttacca gtggctgctg ccagtggcga taagtcgtgt cttaccgggt      3360
tggactcaag acgatagtta ccggataagg cgcagcggtc gggctgaacg ggggggttcgt     3420 gcacacagcc cagcttggag cgaacgacct acaccgaact gagataccta cagcgtgagc      3480
tatgagaaag cgccacgctt cccgaaggga gaaaggcgga caggtatccg gtaagcggca      3540
gggtcggaac aggagagcgc acgagggagc ttccaggggg aaacgcctgg tatctttata      3600
gtcctgtcgg gtttcgccac ctctgacttg agcgtcgatt tttgtgatgc tcgtcagggg      3660
ggcggagcct atggaaaaac gccagcaacg cggccttttt acggttcctg gccttttgct      3720
ggccttttgc tcacatgacc cgaca                                            3745

<210> SEQ ID NO 10
<211> LENGTH: 4746
<212> TYPE: DNA
<213> ORGANISM: Artificial Sequence
<220> FEATURE:
<223> OTHER INFORMATION: Description of Artificial Sequence: Synthetic
      Phage display vector phNGAL102 with CamR used
      as backbone for NNK-Library

<400> SEQUENCE: 10
ccataacgct cggttgccgc cgggcgtttt ttattggcca gatgattaat tcctaatttt        60
tgttgacact ctatcattgg tagagttatt ttaccactcc ctatcagtga tagagaaaag       120
tgaaatgaat agttcgacaa aaatctagat aacgagggca aaaaatgaaa aagacagcta       180
tcgcgattgc agtggctctg ctggcttcg ctaccgtagc gcaggcccag gactccacct        240
cagacctgat cccagcccca cctctgagca aggtccctct gcagcagaac ttccaggaca       300
accaattcca tgggaagtgg tatgtggtag gtctcgcagg gaatgcaatt ctcagagaag       360
acaaagaccc gcaaagatg tatgccacca tctatgagct gaaagaagac aagagctaca       420
atgtcacctc cgtcctgttt aggaaaaaga agtgtgacta ctggatcagg actttttgttc     480 caggttccca gccaggcgag ttcacgctgg caacattaa gagttaccct ggattaacga       540
gttacctcgt ccgagtggtg agcaccaact acaaccagca tgctatggtg ttcttcaaga       600
aagtttctca aaacagggag tacttcaaga tcaccctcta cgggagaacc aaggagctga       660
cttcggaact aaaggagaac ttcatccgct ctctccaaatc tctgggcctc cctgaaaacc      720
acatcgtctt ccctgtccca atcgaccagt gtatcgacgg cagcgctggt ggggcctaga      780
ctgttgaaag ttgtttagca aaaccccata cagaaaattc atttactaac gtctggaaag      840
acgacaaaac tttagatcgt tacgctaact atgagggctg tctgtggaat gctacaggcg      900
ttgtagtttg tactggtgac gaaactcagt gttacggtac atgggttcct attgggcttg      960
ctatccctga aaatgagggt ggtggctctg agggtggcgg ttctgagggt ggcggttctg     1020
agggtggcgg tactaaacct cctgagtacg gtgatacacc tattccgggc tatacttata     1080
```

-continued

```
tcaaccctct cgacggcact tatccgcctg gtactgagca aaaccccgct aatcctaatc    1140
cttctcttga ggagtctcag cctcttaata ctttcatgtt tcagaataat aggttccgaa    1200
ataggcaggg ggcattaact gtttatacgg gcactgttac tcaaggcact gaccccgtta    1260
aaacttatta ccagtacact cctgtatcat caaaagccat gtatgacgct tactggaacg    1320
gtaaattcag agactgcgct ttccattctg gctttaatga ggatccattc gtttgtgaat    1380
atcaaggcca atcgtctgac ctgcctcaac ctcctgtcaa tgctggcggc ggctctggtg    1440
gtggttctgg tggcggctct gagggtggtg gctctgtggg tggcggttct gagggtggcg    1500
gctctgaggg aggcggttcc ggtggtggct ctggttccgg tgattttgat tatgaaaaga    1560
tggcaaacgc taataagggg gctatgaccg aaaatgccga tgaaaacgcg ctacagtctg    1620
acgctaaagg caaacttgat tctgtcgcta ctgattacgg tgctgctatc gatggtttca    1680
ttggtgacgt ttccggcctt gctaatggta atggtgctac tggtgatttt gctggctcta    1740
attcccaaat ggctcaagtc ggtgacggtg ataattcacc tttaatgaat aatttccgtc    1800
aatatttacc ttccctccct caatcggttg aatgtcgccc ttttgtcttt ggcgctggta    1860
aaccatatga ttttctatt gattgtgaca aaataaactt attccgtggt gtctttgcgt    1920 ttctttata tgttgccacc tttatgtatg tattttctac gtttgctaac atactgcgta    1980
ataaggagtc ttaataagct tgacctgtga agtgaaaaat ggcgcacatt gtgcgacatt    2040
ttttttgtct gccgtttacc gctactgcgt cacggatctc cacgcgccct gtagcggcgc    2100
attaagcgcg gcgggtgtgg tggttacgcg cagcgtgacc gctacacttg ccagcgccct    2160
agcgcccgct cctttcgctt tcttcccttc ctttctcgcc acgttcgccg gctttccccg    2220
tcaagctcta aatcggggc tccctttagg gttccgattt agtgctttac ggcacctcga    2280
ccccaaaaaa cttgattagg gtgatggttc acgtagtggg ccatcgccct gatagacggt    2340
ttttcgccct ttgacgttgg agtccacgtt ctttaatagt ggactcttgt tccaaactgg    2400
aacaacactc aaccctatct cggtctattc ttttgattta agggatttt gccgatttc     2460 ggcctattgg ttaaaaaatg agctgattta acaaaatttt aacgcgaatt ttaacaaaat    2520
ttggcgaaaa tgagacgttg atcggcacgt aagaggttcc aactttcacc ataatgaaat    2580
aagatcacta ccgggcgtat ttttgagtt atcgagattt tcaggagcta aggaagctaa    2640
aatggagaaa aaaatcactg gatataccac cgttgatata tcccaatggc atcgtaaaga    2700
acattttgag gcatttcagt cagttgctca atgtacctat aaccagaccg ttcagctgga    2760
tattacggcc ttttttaaga ccgtaaagaa aaataagcac aagttttatc cggcctttat    2820
tcacattctt gcccgcctga tgaatgctca tccggaattc cgtatggcaa tgaaagacgg    2880
tgagctggtg atatgggata gtgttcaccc ttgttacacc gttttccatg agcaaactga    2940
aacgttttca tcgctctgga gtgaatacca cgacgatttc cggcagtttc tacacatata    3000
ttcgcaagat gtggcgtgtt acggtgaaaa cctggcctat ttccctaaag ggtttattga    3060
gaatatgttt ttcgtctcag ccaatccctg ggtgagtttc accagttttg atttaaacgt    3120
ggccaatatg gacaacttct tcgcccccgt tttcactatg gcaaatatt atacgcaagg    3180 cgacaaggtg ctgatgccgc tggcgattca ggttcatcat gccgtttgtg atggcttcca    3240
tgtcggcaga atgcttaatg aattacaaca gtactgcgat gagtggcagg gcggggcgta    3300
ataggaatta tgatgtctc gtttagataa agtaaagtg attaacacgc cattagagct    3360
gcttaatgag gtcggaatcg aaggtttaac aacccgtaaa ctcgcccaga agctaggtgt    3420
agagcagcct acattgtatt ggcatgtaaa aaataagcgg gctttgctcg acgccttagc    3480
```

```
cattgagatg ttagataggc accatactca cttttgccct ttagaagggg aaagctggca   3540 agattttta  cgtaataacg ctaaaagttt tagatgtgct ttactaagtc atcgcgatgg   3600
agcaaaagta catttaggta cacggcctac agaaaaacag tatgaaactc tcgaaaatca   3660
attagccttt ttatgccaac aaggttttc  actagagaat gcattatatg cactcagcgc   3720
agtggggcat tttactttag gttgcgtatt ggaagatcaa gagcatcaag tcgctaaaga   3780
agaaagggaa acacctacta ctgatagtat gccgccatta ttacgacaag ctatcgaatt   3840
atttgatcac caaggtgcag agccagcctt cttattcggc cttgaattga tcatatgcgg   3900
attagaaaaa caacttaaat gtgaaagtgg gtcttaaaag cagcataacc ttttccgtg    3960 atggtaactt cactagttta aaaggatcta ggtgaagatc cttttttgata atctcatgac   4020 caaaatccct aacgtgagt  tttcgttcca ctgagcgtca gaccccgtag aaaagatcaa   4080
aggatcttct tgagatcctt ttttttctgcg cgtaatctgc tgcttgcaaa caaaaaaacc   4140
accgctacca gcggtggttt gtttgccgga tcaagagcta ccaactcttt ttccgaaggt   4200
aactggcttc agcagagcgc agataccaaa tactgttctt ctagtgtagc cgtagttagg   4260
ccaccacttc aagaactctg tagcaccgcc tacatacctc gctctgctaa tcctgttacc   4320
agtggctgct gccagtggcg ataagtcgtg tcttaccggg ttggactcaa gacgatagtt   4380
accggataag gcgcagcggt cgggctgaac ggggggttcg tgcacacagc ccagcttgga   4440
gcgaacgacc tacaccgaac tgagatacct acagcgtgag ctatgagaaa gcgccacgct   4500
tcccgaaggg agaaaggcgg acaggtatcc ggtaagcggc agggtcggaa caggagagcg   4560
cacgagggag cttccagggg gaaacgcctg gtatctttat agtcctgtcg ggtttcgcca   4620
cctctgactt gagcgtcgat ttttgtgatg ctcgtcaggg gggcggagcc tatggaaaaa   4680
cgccagcaac gcggcctttt tacggttcct ggccttttgc tggccttttg ctcacatgac   4740
ccgaca                                                              4746
```

<210> SEQ ID NO 11
<211> LENGTH: 4963
<212> TYPE: DNA
<213> ORGANISM: Artificial Sequence
<220> FEATURE:
<223> OTHER INFORMATION: Description of Artificial Sequence: Synthetic
      Phage display vector phNGAL108 with AmpR used
      for Cloning Library

<400> SEQUENCE: 11

```
ccatcgaatg gccagatgat taattcctaa ttttttgttga cactctatca ttgatagagt     60
tattttacca ctccctatca gtgatagaga aagtgaaat  gaatagttcg acaaaaatct    120
agataacgag ggcaaaaaat gaaaagaca  gctatcgcga ttgcagtggc tctggctggc    180
ttcgctaccg tagcgcaggc ccaggactcc acctcagacc tgatcccagc cccacctctg    240
agcaaggtcc ctctgcagca gaacttccag gacaaccaat tccatgggaa gtggtatgtg    300
gtaggtctcg cagggaatgc aattctcaga gaagacaaag acccgcaaaa gatgtatgcc    360
accatctatg agctgaaaga agacaagagc tacaatgtca cctccgtcct gtttaggaaa    420
aagaagtgtg actactggat caggactttt gttccaggtt cccagccagg cgagttcacg    480
ctgggcaaca ttaagagtta ccctggatta acgagttacc tcgtccgagt ggtgagcacc    540
aactacaacc agcatgctat ggtgttcttc aagaaagttt ctcaaaacag ggagtacttc    600
aagatcaccc tctacgggag aaccaaggag ctgacttcgg aactaaagga aacttcatc    660 cgcttctcca atctctgggg cctccctgaa aaccacatcg tcttccctgt cccaatcgac    720
```

```
cagtgtatcg acggcagcgc ttggcgtcac ccgcagttcg gtggggccta gactgttgaa    780
agttgtttag caaaacccca tacagaaaat tcatttacta acgtctggaa agacgacaaa    840
actttagatc gttacgctaa ctatgagggc tgtctgtgga atgctacagg cgttgtagtt    900
tgtactggtg acgaaactca gtgttacggt acatgggttc ctattgggct tgctatccct    960
gaaaatgagg gtggtggctc tgagggtggc ggttctgagg gtggcggttc tgagggtggc   1020
ggtactaaac ctcctgagta cggtgataca cctattccgg gctatactta tatcaaccct   1080
ctcgacggca cttatccgcc tggtactgag caaaaccccg ctaatcctaa tccttctctt   1140
gaggagtctc agcctcttaa tactttcatg tttcagaata taggttccg aaataggcag    1200
ggggcattaa ctgtttatac gggcactgtt actcaaggca ctgaccccgt taaaacttat   1260
taccagtaca ctcctgtatc atcaaaagcc atgtatgacg cttactggaa cggtaaattc   1320
agagactgcg ctttccattc tggctttaat gaggatccat tcgtttgtga atatcaaggc   1380
caatcgtctg acctgcctca acctcctgtc aatgctggcg gcggctctgg tggtggttct   1440
ggtggcggct ctgagggtgg tggctctgag ggtggcggtt ctgagggtgg cggctctgag   1500
ggaggcggtt ccggtggtgg ctctggttcc ggtgattttg attatgaaaa gatggcaaac   1560
gctaataagg gggctatgac cgaaaatgcc gatgaaaacg cgctacagtc tgacgctaaa   1620
ggcaaacttg attctgtcgc tactgattac ggtgctgcta tcgatggttt cattggtgac   1680
gtttccggcc ttgctaatgg taatggtgct actggtgatt tgctggctc taattcccaa    1740
atggctcaag tcggtgacgg tgataattca cctttaatga ataatttccg tcaatattta   1800
ccttccctcc ctcaatcggt tgaatgtcgc ccttttgtct ttggcgctgg taaaccatat   1860
gaattttcta ttgattgtga caaaataaac ttattccgtg gtgtctttgc gtttctttta   1920
tatgttgcca cctttatgta tgtatttcct acgtttgcta acatactgcg taataaggag   1980
tcttaataag cttgacctgt gaagtgaaaa atggcgcaca ttgtgcgaca tttttttgt    2040
ctgccgttta ccgctactgc gtcacggatc tccacgcgcc ctgtagcggc gcattaagcg   2100
cggcgggtgt ggtggttacg cgcagcgtga ccgctacact tgccagcgcc ctagcgcccg   2160
ctcctttcgc tttcttccct tcctttctcg ccacgttcgc cggctttccc cgtcaagctc   2220
taaatcgggg gctcccttta gggttccgat ttagtgcttt acggcacctc gaccccaaaa   2280
aacttgatta gggtgatggt tcacgtagtg gccatcgcc ctgatagacg gttttcgcc    2340
ctttgacgtt ggagtccacg ttctttaata gtggactctt gttccaaact ggaacaacac   2400
tcaaccctat ctcggtctat tcttttgatt tataagggat tttgccgatt tcggcctatt   2460
ggttaaaaaa tgagctgatt taacaaaaat ttaacgcgaa ttttaacaaa atattaacgc   2520
ttacaatttc aggtggcact tttcggggaa atgtgcgcgg aacccctatt tgtttatttt   2580
tctaaataca ttcaaatatg tatccgctca tgagacaata accctgataa atgcttcaat   2640
aatattgaaa aaggaagagt atgagtattc aacatttccg tgtcgccctt attccctttt   2700
ttgcggcatt ttgccttcct gtttttgctc acccagaaac gctggtgaaa gtaaaagatg   2760
ctgaagatca gttgggtgca cgagtgggtt acatcgaact ggatctcaac agcggtaaga   2820
tccttgagag ttttcgcccc gaagaacgtt ttccaatgat gagcactttt aaagttctgc   2880
tatgtggcgc ggtattatcc cgtattgacg ccgggcaaga gcaactcggt cgccgcatac   2940
actattctca gaatgacttg gttgagtact caccagtcac agaaaagcat cttacggatg   3000
gcatgacagt aagagaatta tgcagtgctg ccataaccat gagtgataac actgcggcca   3060
acttacttct gacaacgatc ggaggaccga aggagctaac cgcttttttg cacaacatgg   3120
```

-continued

```
gggatcatgt aactcgcctt gatcgttggg aaccggagct gaatgaagcc ataccaaacg    3180
acgagcgtga caccacgatg cctgtagcaa tggcaacaac gttgcgcaaa ctattaactg    3240
gcgaactact tactctagct tcccggcaac aattgataga ctggatggag gcggataaag    3300
ttgcaggacc acttctgcgc tcggcccttc cggctggctg gtttattgct gataaatctg    3360
gagccggtga gcgtggctct cgcggtatca ttgcagcact ggggccagat ggtaagccct    3420
cccgtatcgt agttatctac acgacgggga gtcaggcaac tatggatgaa cgaaatagac    3480
agatcgctga gataggtgcc tcactgatta agcattggta ggaattaatg atgtctcgtt    3540
tagataaaag taaagtgatt aacagcgcat tagagctgct taatgaggtc ggaatcgaag    3600
gtttaacaac ccgtaaactc gcccagaagc taggtgtaga gcagcctaca ttgtattggc    3660
atgtaaaaaa taagcgggct tgctcgacg ccttagccat tgagatgtta gataggcacc    3720
atactcactt tgcccttta aaggggaaa gctggcaaga tttttacgt aataacgcta    3780 aaagttttag atgtgcttta ctaagtcatc gcgatggagc aaaagtacat ttaggtacac    3840
ggcctacaga aaacagtat gaaactctcg aaaatcaatt agccttttta tgccaacaag    3900 gttttttcact agagaatgca ttatatgcac tcagcgcagt ggggcatttt actttaggtt    3960
gcgtattgga agatcaagag catcaagtcg ctaaagaaga aagggaaaca cctactactg    4020
atagtatgcc gccattatta cgacaagcta tcgaattatt tgatcaccaa ggtgcagagc    4080
cagccttctt attcggcctt gaattgatca tatgcgatt agaaaaacaa cttaaatgtg    4140
aaagtgggtc ttaaaagcag cataaccttt ttccgtgatg gtaacttcac tagtttaaaa    4200
ggatctaggt gaagatcctt tttgataatc tcatgaccaa aatcccttaa cgtgagtttt    4260
cgttccactg agcgtcagac cccgtagaaa agatcaaagg atcttcttga gatccttttt    4320
ttctgcgcgt aatctgctgc ttgcaaacaa aaaaaccacc gctaccagcg gtggtttgtt    4380
tgccggatca gagctaccaa actctttttc cgaaggtaac tggcttcagc agagcgcaga    4440
taccaaatac tgtccttcta gtgtagccgt agttaggcca ccacttcaag aactctgtag    4500
caccgcctac atacctcgct ctgctaatcc tgttaccagt ggctgctgcc agtggcgata    4560
agtcgtgtct taccgggttg gactcaagac gatagttacc ggataaggcg cagcggtcgg    4620
gctgaacggg gggttcgtgc acacagccca gcttggagcg aacgacctac accgaactga    4680
gatacctaca gcgtgagcta tgagaaagcg ccacgcttcc cgaagggaga aaggcggaca    4740
ggtatccggt aagcggcagg gtcggaacag gagagcgcac gagggagctt ccaggggaa    4800 acgcctggta tctttatagt cctgtcgggt ttcgccacct ctgacttgag cgtcgatttt    4860
tgtgatgctc gtcaggggggg cggagcctat ggaaaaacgc cagcaacgcg gccttttac    4920 ggttcctggc cttttgctgg cctttgctc acatgacccg aca                      4963
```

<210> SEQ ID NO 12
<211> LENGTH: 197
<212> TYPE: PRT
<213> ORGANISM: Artificial Sequence
<220> FEATURE:
<223> OTHER INFORMATION: Description of Artificial Sequence: Synthetic
      hNGAL with T7 tag encoded by phNGAL 101 polypeptide

<400> SEQUENCE: 12

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

```
Val Val Gly Leu Ala Gly Asn Ala Ile Leu Arg Glu Asp Lys Asp Pro
         35                  40                  45

Gln Lys Met Tyr Ala Thr Ile Tyr Glu Leu Lys Glu Asp Lys Ser Tyr
 50                  55                  60

Asn Val Thr Ser Val Leu Phe Arg Lys Lys Cys Asp Tyr Trp Ile
 65                  70                  75                  80

Arg Thr Phe Val Pro Gly Ser Gln Pro Gly Glu Phe Thr Leu Gly Asp
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Thr Val Ser Gln
            115                 120                 125

Asn Arg Glu Tyr Phe Lys Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Met Ala Ser Met Thr Gly
                180                 185                 190

Gly Gln Gln Met Gly
            195
```

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer (ASKD20)

<400> SEQUENCE: 13
ccactcccta tcagtgat                                                 18

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer (NGAL67)

<400> SEQUENCE: 14
cttcacaggt caagcttatt attttcgaa c                                  31

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer (3004-Slo1 bio)

<400> SEQUENCE: 15
ccaggacaac caattccatg ggaaatggta tgtcgtgggc                         40

<210> SEQ ID NO 16
<211> LENGTH: 88
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g or t
<220> FEATURE:
<221> NAME/KEY: modified_base
<222> LOCATION: (32)..(33)
<223> OTHER INFORMATION: a, c, g or t
<220> FEATURE:
<221> NAME/KEY: modified_base
<222> LOCATION: (35)..(36)
<223> OTHER INFORMATION: a, c, g or t
<220> FEATURE:
<221> NAME/KEY: modified_base
<222> LOCATION: (59)..(60)
<223> OTHER INFORMATION: a, c, g or t
<220> FEATURE:
<221> NAME/KEY: modified_base
<222> LOCATION: (68)..(69)
<223> OTHER INFORMATION: a, c, g or t

<400> SEQUENCE: 16
gaagtggtat gtggtaggtn nkgcagggaa tnnknnkctc agagaagaca aagacccgnn      60
kaagatgnnk gccaccatct atgagctg                                        88

<210> SEQ ID NO 17
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: a, c, g or t
<220> FEATURE:
<221> NAME/KEY: modified_base
<222> LOCATION: (26)..(27)
<223> OTHER INFORMATION: a, c, g or t
<220> FEATURE:
<221> NAME/KEY: modified_base
<222> LOCATION: (32)..(33)
<223> OTHER INFORMATION: a, c, g or t
<220> FEATURE:
<221> NAME/KEY: modified_base
<222> LOCATION: (35)..(36)
<223> OTHER INFORMATION: a, c, g or t
<220> FEATURE:
<221> NAME/KEY: modified_base
<222> LOCATION: (47)..(48)
<223> OTHER INFORMATION: a, c, g or t
<220> FEATURE:
<221> NAME/KEY: modified_base
<222> LOCATION: (53)..(54)
<223> OTHER INFORMATION: a, c, g or t
<220> FEATURE:
<221> NAME/KEY: modified_base
<222> LOCATION: (59)..(60)
<223> OTHER INFORMATION: a, c, g or t

<400> SEQUENCE: 17
caagagctac aatgtcaccn nkgtcnnktt tnnknnkaag aagtgtnnkt acnnkatcnn      60
kacttttgtt ccaggttcc                                                  79

<210> SEQ ID NO 18
<211> LENGTH: 68
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g or t
<220> FEATURE:
<221> NAME/KEY: modified_base
<222> LOCATION: (31)..(32)
<223> OTHER INFORMATION: a, c, g or t
<220> FEATURE:
<221> NAME/KEY: modified_base
<222> LOCATION: (40)..(41)
<223> OTHER INFORMATION: a, c, g or t
<220> FEATURE:
<221> NAME/KEY: modified_base
<222> LOCATION: (49)..(50)
<223> OTHER INFORMATION: a, c, g or t

<400> SEQUENCE: 18
ggcgagttca cgctgggcnn kattaagagt nnkcctggan nkacgagtnn kctcgtccga    60
gtggtgag                                                            68

<210> SEQ ID NO 19
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(20)
<223> OTHER INFORMATION: a, c, g or t
<220> FEATURE:
<221> NAME/KEY: modified_base
<222> LOCATION: (25)..(26)
<223> OTHER INFORMATION: a, c, g or t
<220> FEATURE:
<221> NAME/KEY: modified_base
<222> LOCATION: (40)..(41)
<223> OTHER INFORMATION: a, c, g or t
<220> FEATURE:
<221> NAME/KEY: modified_base
<222> LOCATION: (46)..(47)
<223> OTHER INFORMATION: a, c, g or t

<400> SEQUENCE: 19
gctatggtgt tcttcaagnn kgttnnkcaa aacagggagn nkttcnnkat caccctctac    60
gggagaac                                                            68

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 20
ggtgacattg tagctcttgt cttctttcag ctcatagatg gtggc                   45

<210> SEQ ID NO 21
<211> LENGTH: 42
<212> TYPE: DNA
<213> ORGANISM: Artificial Sequence
```

```
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 21
gcccagcgtg aactcgcctg gctgggaacc tggaacaaaa gt                    42

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 22
cttgaagaac accatagcat gctggttgta gttggtgctc accactcgga cgag        54

<210> SEQ ID NO 23
<211> LENGTH: 64
<212> TYPE: DNA
<213> ORGANISM: Artificial Sequence
<220> FEATURE:
<223> OTHER INFORMATION: Description of Artificial Sequence: Synthetic
      PCR-Primer with fixed nucleotide sequences
      corresponding to the non-coding strand

<400> SEQUENCE: 23
ggagaagcgg atgaagttct cctttagttc cgaagtcagc tccttggttc tcccgtagag  60
ggtg                                                              64

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' flanking PCR-Oligo biotinylated

<400> SEQUENCE: 24
ccaggacaac caattccatg ggaagtggta tgtggtaggt                        40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' flanking PCR-Oligo biotinylated

<400> SEQUENCE: 25
ttcagggagg cccagagatt tggagaagcg gatgaagttc                        40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: 3' flanking PCR-Oligo biotinylated for Sloning
      Fragment

<400> SEQUENCE: 26
ttcagggagg cccagagatt tggaaaagcg gataaaattt                                40

<210> SEQ ID NO 27
<211> LENGTH: 178
<212> TYPE: PRT
<213> ORGANISM: Homo sapiens
<220> FEATURE:
<223> OTHER INFORMATION: wt Lcn2 (hNGAL)

<400> SEQUENCE: 27
```

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

```
<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 28
ccannnnnnt gg                                                              12

<210> SEQ ID NO 29
<211> LENGTH: 20
<212> TYPE: PRT
<213> ORGANISM: Homo sapiens
```

```
<400> SEQUENCE: 29

Met Pro Leu Gly Leu Leu Trp Leu Gly Leu Ala Leu Leu Gly Ala Leu
1               5                   10                  15

His Ala Gln Ala
            20

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 30

His His His His His
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cccaggactc cacctcagac c                                              21

<210> SEQ ID NO 33
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(564)

<400> SEQUENCE: 33 cag gac tcc acc tca gac ctg atc cca gcc cca cct ctg agc aag gtc    48
Gln Asp Ser Thr Ser Asp Leu Ile Pro Ala Pro Pro Leu Ser Lys Val
1               5                   10                  15 cct ctg cag cag aac ttc cag gac aac caa ttc cat ggg aag tgg tat    96
Pro Leu Gln Gln Asn Phe Gln Asp Asn Gln Phe His Gly Lys Trp Tyr
            20                  25                  30 gtg gta ggt ctc gca ggg aat gca att ctc aga gaa gac aaa gac ccg   144
Val Val Gly Leu Ala Gly Asn Ala Ile Leu Arg Glu Asp Lys Asp Pro
        35                  40                  45 caa aag atg tat gcc acc atc tat gag ctg aaa gaa gac aag agc tac   192
Gln Lys Met Tyr Ala Thr Ile Tyr Glu Leu Lys Glu Asp Lys Ser Tyr
    50                  55                  60
```

```
aat gtc acc tcc gtc ctg ttt agg aaa aag aag tgt gac tac tgg atc       240
Asn Val Thr Ser Val Leu Phe Arg Lys Lys Lys Cys Asp Tyr Trp Ile
 65              70                  75                  80 agg act ttt gtt cca ggt tcc cag cca ggc gag ttc acg ctg ggc aac       288
Arg Thr Phe Val Pro Gly Ser Gln Pro Gly Glu Phe Thr Leu Gly Asn
                 85                  90                  95 att aag agt tac cct gga tta acg agt tac ctc gtc cga gtg gtg agc       336
Ile Lys Ser Tyr Pro Gly Leu Thr Ser Tyr Leu Val Arg Val Val Ser
            100                 105                 110 acc aac tac aac cag cat gct atg gtg ttc ttc aag aaa gtt tct caa       384
Thr Asn Tyr Asn Gln His Ala Met Val Phe Phe Lys Lys Val Ser Gln
        115                 120                 125 aac agg gag tac ttc aag atc acc ctc tac ggg aga acc aag gag ctg       432
Asn Arg Glu Tyr Phe Lys Ile Thr Leu Tyr Gly Arg Thr Lys Glu Leu
    130                 135                 140 act tcg gaa cta aag gag aac ttc atc cgc ttc tcc aaa tct ctg ggc       480
Thr Ser Glu Leu Lys Glu Asn Phe Ile Arg Phe Ser Lys Ser Leu Gly
145                 150                 155                 160 ctc cct gaa aac cac atc gtc ttc cct gtc cca atc gac cag tgt atc       528
Leu Pro Glu Asn His Ile Val Phe Pro Val Pro Ile Asp Gln Cys Ile
                165                 170                 175 gac ggc agc gct tgg tcc cac ccg cag ttc gaa aaa taa                   567
Asp Gly Ser Ala Trp Ser His Pro Gln Phe Glu Lys
            180                 185

<210> SEQ ID NO 34
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
 65                  70                  75                  80

Arg Thr Phe Val Pro Gly Ser Gln Pro Gly Glu Phe Thr Leu Gly Asn
                 85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 35
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
ttattttcg aactgcgggt gggaccaagc gctgccgtcg atacactggt cgattgggac    60
agggaagacg atgtggtttt cagggaggcc cagagatttg gagaagcgga tgaagttctc   120
ctttagttcc gaagccagct ccttggttct cccgtagagg gtgatcttga agtactccct   180
gttttgagaa actttcttga agaacaccat agcatgctgg ttgtagttgg tgctcaccac   240
tcggacgagg taactcgtta atccagggta actcttaatg ttgcccagcg tgaactcgcc   300
tggctgggaa cctggaacaa aagtcctgat ccagtagtca cacttctttt tcctaaacag   360
gacggaggtg acattgtagc tcttgtcttc tttcagctca tagatggtgg catacatctt   420
ttgcgggtct ttgtcttctc tgagaattgc attccctgcg agacctacca cataccactt   480
cccatggaat tggttgtcct ggaagttctg ctgcagaggg accttgctca gaggtggggc   540
tgggatcagg tctgaggtgg agtcctg                                       567
```

<210> SEQ ID NO 36
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (59)..(60)
<223> OTHER INFORMATION: a, c, t, g, unknown or other

<400> SEQUENCE: 36

```
caagagctac aatgtcacan nkgtcnnktt tnnknnkaag aagtgtnnkt acnnkatcnn    60
kacttttgtt ccaggttcc                                                 79
```

<210> SEQ ID NO 37
<211> LENGTH: 45
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 37
ggtgacattg tagctcttat cttctttcag ctcatagatg gtggc                    45

<210> SEQ ID NO 38
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggagaagcgg atgaagttct cctttagttc cgaagccagc tccttggttc tcccgtagag    60
ggtg                                                                 64

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
actgcgggtg ggaccaagcg ctgccgt                                        27

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ala Trp Ser His Pro Gln Phe Glu Lys
1               5                   10

<210> SEQ ID NO 41
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (2)..(403)
<220> FEATURE:
<221> NAME/KEY: modified_base
<222> LOCATION: (32)..(34)
<223> OTHER INFORMATION: a, c, g or t
<220> FEATURE:
<221> NAME/KEY: modified_base
<222> LOCATION: (44)..(49)
<223> OTHER INFORMATION: a, c, g or t
<220> FEATURE:
<221> NAME/KEY: modified_base
<222> LOCATION: (71)..(73)
<223> OTHER INFORMATION: a, c, g or t
<220> FEATURE:
<221> NAME/KEY: modified_base
<222> LOCATION: (80)..(82)
<223> OTHER INFORMATION: a, c, g or t
```

```
<220> FEATURE:
<221> NAME/KEY: modified_base
<222> LOCATION: (128)..(130)
<223> OTHER INFORMATION: a, c, g or t
<220> FEATURE:
<221> NAME/KEY: modified_base
<222> LOCATION: (134)..(136)
<223> OTHER INFORMATION: a, c, g or t
<220> FEATURE:
<221> NAME/KEY: modified_base
<222> LOCATION: (140)..(145)
<223> OTHER INFORMATION: a, c, g or t
<220> FEATURE:
<221> NAME/KEY: modified_base
<222> LOCATION: (155)..(157)
<223> OTHER INFORMATION: a, c, g or t
<220> FEATURE:
<221> NAME/KEY: modified_base
<222> LOCATION: (161)..(163)
<223> OTHER INFORMATION: a, c, g or t
<220> FEATURE:
<221> NAME/KEY: modified_base
<222> LOCATION: (167)..(169)
<223> OTHER INFORMATION: a, c, g or t
<220> FEATURE:
<221> NAME/KEY: modified_base
<222> LOCATION: (212)..(214)
<223> OTHER INFORMATION: a, c, g or t
<220> FEATURE:
<221> NAME/KEY: modified_base
<222> LOCATION: (224)..(226)
<223> OTHER INFORMATION: a, c, g or t
<220> FEATURE:
<221> NAME/KEY: modified_base
<222> LOCATION: (233)..(235)
<223> OTHER INFORMATION: a, c, g or t
<220> FEATURE:
<221> NAME/KEY: modified_base
<222> LOCATION: (242)..(244)
<223> OTHER INFORMATION: a, c, g or t
<220> FEATURE:
<221> NAME/KEY: modified_base
<222> LOCATION: (299)..(301)
<223> OTHER INFORMATION: a, c, g or t
<220> FEATURE:
<221> NAME/KEY: modified_base
<222> LOCATION: (305)..(307)
<223> OTHER INFORMATION: a, c, g or t
<220> FEATURE:
<221> NAME/KEY: modified_base
<222> LOCATION: (320)..(322)
<223> OTHER INFORMATION: a, c, g or t
<220> FEATURE:
<221> NAME/KEY: modified_base
<222> LOCATION: (326)..(328)
<223> OTHER INFORMATION: a, c, g or t

<400> SEQUENCE: 41 c caa ttc cat ggg aaa tgg tat gtc gtg ggc nnn gcc gga aat nnn nnn      49
  Gln Phe His Gly Lys Trp Tyr Val Val Gly Xaa Ala Gly Asn Xaa Xaa
  1               5                   10                  15 ctg cgt gag gat aag gat ccg nnn aaa atg nnn gcg acc att tac gag        97
Leu Arg Glu Asp Lys Asp Pro Xaa Lys Met Xaa Ala Thr Ile Tyr Glu
             20                  25                  30 ttg aaa gaa gat aaa tca tat aac gtc acc nnn gtg nnn ttt nnn nnn       145
Leu Lys Glu Asp Lys Ser Tyr Asn Val Thr Xaa Val Xaa Phe Xaa Xaa
         35                  40                  45 aag aaa tgc nnn tac nnn att nnn acc ttt gtg ccg ggg agc cag ccg       193
Lys Lys Cys Xaa Tyr Xaa Ile Xaa Thr Phe Val Pro Gly Ser Gln Pro
     50                  55                  60 ggc gag ttt act tta ggc nnn att aaa agt nnn ccg ggc nnn aca tca       241
Gly Glu Phe Thr Leu Gly Xaa Ile Lys Ser Xaa Pro Gly Xaa Thr Ser
 65                  70                  75                  80
```

```
nnn ttg gtc cgc gtc gtg agc acc aac tac aac cag cat gcc atg gtg      289
Xaa Leu Val Arg Val Val Ser Thr Asn Tyr Asn Gln His Ala Met Val
             85                  90                  95 ttc ttc aag nnn gtg nnn cag aac cgc gag nnn ttt nnn atc aca ctg      337
Phe Phe Lys Xaa Val Xaa Gln Asn Arg Glu Xaa Phe Xaa Ile Thr Leu
            100                 105                 110 tac ggg cgc acg aaa gaa ctg aca agc gag ctg aag gaa aat ttt atc      385
Tyr Gly Arg Thr Lys Glu Leu Thr Ser Glu Leu Lys Glu Asn Phe Ile
            115                 120                 125 cgc ttt tcc aaa tct ctg g                                            404
Arg Phe Ser Lys Ser Leu
        130

<210> SEQ ID NO 42
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (11)..(11)
<223> OTHER INFORMATION: Any amino acid
<220> FEATURE:
<221> NAME/KEY: misc_feature
<222> LOCATION: (15)..(15)
<223> OTHER INFORMATION: Any amino acid
<220> FEATURE:
<221> NAME/KEY: misc_feature
<222> LOCATION: (16)..(16)
<223> OTHER INFORMATION: Any amino acid
<220> FEATURE:
<221> NAME/KEY: misc_feature
<222> LOCATION: (24)..(24)
<223> OTHER INFORMATION: Any amino acid
<220> FEATURE:
<221> NAME/KEY: misc_feature
<222> LOCATION: (27)..(27)
<223> OTHER INFORMATION: Any amino acid
<220> FEATURE:
<221> NAME/KEY: misc_feature
<222> LOCATION: (43)..(43)
<223> OTHER INFORMATION: Any amino acid
<220> FEATURE:
<221> NAME/KEY: misc_feature
<222> LOCATION: (45)..(45)
<223> OTHER INFORMATION: Any amino acid
<220> FEATURE:
<221> NAME/KEY: misc_feature
<222> LOCATION: (47)..(47)
<223> OTHER INFORMATION: Any amino acid
<220> FEATURE:
<221> NAME/KEY: misc_feature
<222> LOCATION: (48)..(48)
<223> OTHER INFORMATION: Any amino acid
<220> FEATURE:
<221> NAME/KEY: misc_feature
<222> LOCATION: (52)..(52)
<223> OTHER INFORMATION: Any amino acid
<220> FEATURE:
<221> NAME/KEY: misc_feature
<222> LOCATION: (54)..(54)
<223> OTHER INFORMATION: Any amino acid
<220> FEATURE:
<221> NAME/KEY: misc_feature
<222> LOCATION: (56)..(56)
<223> OTHER INFORMATION: Any amino acid
<220> FEATURE:
<221> NAME/KEY: misc_feature
<222> LOCATION: (71)..(71)
<223> OTHER INFORMATION: Any amino acid
```

```
<220> FEATURE:
<221> NAME/KEY: misc_feature
<222> LOCATION: (75)..(75)
<223> OTHER INFORMATION: Any amino acid
<220> FEATURE:
<221> NAME/KEY: misc_feature
<222> LOCATION: (78)..(78)
<223> OTHER INFORMATION: Any amino acid
<220> FEATURE:
<221> NAME/KEY: misc_feature
<222> LOCATION: (81)..(81)
<223> OTHER INFORMATION: Any amino acid
<220> FEATURE:
<221> NAME/KEY: misc_feature
<222> LOCATION: (100)..(100)
<223> OTHER INFORMATION: Any amino acid
<220> FEATURE:
<221> NAME/KEY: misc_feature
<222> LOCATION: (102)..(102)
<223> OTHER INFORMATION: Any amino acid
<220> FEATURE:
<221> NAME/KEY: misc_feature
<222> LOCATION: (107)..(107)
<223> OTHER INFORMATION: Any amino acid
<220> FEATURE:
<221> NAME/KEY: misc_feature
<222> LOCATION: (109)..(109)
<223> OTHER INFORMATION: Any amino acid

<400> SEQUENCE: 42

Gln Phe His Gly Lys Trp Tyr Val Val Gly Xaa Ala Gly Asn Xaa Xaa
1               5                   10                  15

Leu Arg Glu Asp Lys Asp Pro Xaa Lys Met Xaa Ala Thr Ile Tyr Glu
            20                  25                  30

Leu Lys Glu Asp Lys Ser Tyr Asn Val Thr Xaa Val Xaa Phe Xaa Xaa
        35                  40                  45

Lys Lys Cys Xaa Tyr Xaa Ile Xaa Thr Phe Val Pro Gly Ser Gln Pro
    50                  55                  60

Gly Glu Phe Thr Leu Gly Xaa Ile Lys Ser Xaa Pro Gly Xaa Thr Ser
65              70                  75                  80

Xaa Leu Val Arg Val Val Ser Thr Asn Tyr Asn Gln His Ala Met Val
                85                  90                  95

Phe Phe Lys Xaa Val Xaa Gln Asn Arg Glu Xaa Phe Xaa Ile Thr Leu
                100                 105                 110

Tyr Gly Arg Thr Lys Glu Leu Thr Ser Glu Leu Lys Glu Asn Phe Ile
        115                 120                 125

Arg Phe Ser Lys Ser Leu
            130

<210> SEQ ID NO 43
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
ccagagattt ggaaaagcgg ataaaatttt ccttcagctc gcttgtcagt tctttcgtgc      60 gccccgtacag tgtgatctta agtactcgc ggttctggga cactttcttg aagaacacca    120
tggcatgctg gttgtagttg gtgctcacga cgcggaccaa gtatgatgtc aggcccgggt    180
aacttttaat gttgcctaaa gtaaactcgc ccggctggct ccccggcaca aaggtacgaa    240
tccagtagtc gcatttcttt ttgcgaaaca acacggaggt gacgttatat gatttatctt    300
```

```
ctttcaactc gtaaatggtc gcatacattt tctgcggatc cttatcctca cgcagaatgg    360
catttccggc caggcccacg acataccatt tcccatggaa ttgg                     404
```

<210> SEQ ID NO 44
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 45
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Trp Ile Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Arg Val Arg Phe Asp Glu Lys Lys Cys Gly Tyr Gly Ile
65                  70                  75                  80

Ala Thr Phe Val Pro Gly Ser Gln Pro Gly Glu Phe Thr Leu Gly Val
                85                  90                  95
```

```
Ile Lys Ser Arg Pro Gly Ile Thr Ser Asp Leu Val Arg Val Val Ser
            100                 105                 110

Thr Asn Tyr Asn Gln His Ala Met Val Phe Phe Lys Phe Val Lys Gln
            115                 120                 125

Asn Arg Glu Tyr Phe Gly Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 46
<211> LENGTH: 188
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Val Ala Gly Asn Ala Met Leu Arg Glu Asp Lys Asp Pro
            35                  40                  45

Leu Lys Met Arg Ala Thr Ile Tyr Glu Leu Lys Glu Asp Lys Ser Tyr
50                  55                  60

Asn Val Thr Gly Val Ser Phe Trp Arg Lys Lys Cys His Tyr Lys Ile
65                  70                  75                  80

Gly Thr Phe Val Pro Gly Ser Gln Pro Gly Glu Phe Thr Leu Gly Asp
                85                  90                  95

Ile Lys Ser Gly Pro Gly Gln Thr Ser Asn Leu Val Arg Val Val Ser
            100                 105                 110

Thr Asn Tyr Asn Gln His Ala Met Val Phe Phe Lys Glu Val Arg Gln
            115                 120                 125

Asn Arg Glu Trp Phe Ala Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```

<210> SEQ ID NO 47
<211> LENGTH: 188
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 47

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Arg Ala Gly Asn Val Ala Leu Arg Glu Asp Lys Asp Pro
        35                  40                  45

Pro Lys Met Arg Ala Thr Ile Tyr Glu Leu Lys Glu Asp Lys Ser Tyr
    50                  55                  60

Asn Val Thr Asn Val Arg Phe Ala Met Lys Lys Cys Met Tyr Ser Ile
65                  70                  75                  80

Gly Thr Phe Val Pro Gly Ser Gln Pro Gly Glu Phe Thr Leu Gly Gln
                85                  90                  95

Ile Lys Ser Glu Pro Gly Asn Thr Ser Asn Leu Val Arg Val Val Ser
            100                 105                 110

Thr Asn Tyr Asn Gln His Ala Met Val Phe Phe Lys Glu Val Tyr Gln
        115                 120                 125

Asn Arg Glu Ile Phe Phe Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 48
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Ala Arg Leu Arg Glu Asp Lys Asp Pro
        35                  40                  45

Val Lys Met Thr Ala Thr Ile Tyr Glu Leu Lys Glu Asp Lys Ser Tyr
    50                  55                  60

Asn Val Thr Ala Val Gln Phe Arg Leu Lys Lys Cys Gln Tyr Gly Ile
65                  70                  75                  80

Thr Thr Phe Val Pro Gly Ser Gln Pro Gly Glu Phe Thr Leu Gly Asp
                85                  90                  95

Ile Lys Ser Ile Pro Gly Leu Thr Ser Met Leu Val Arg Val Val Ser
            100                 105                 110

Thr Asn Tyr Asn Gln His Ala Met Val Phe Phe Lys Arg Val Arg Gln
        115                 120                 125

Asn Arg Glu Phe Phe Asp Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

-continued

Leu Pro Glu Asn His Ile Val Phe Pro Val Pro Ile Asp Gln Cys Ile
            165                 170                 175

Asp Gly Ser Ala Trp Ser His Pro Gln Phe Glu Lys
        180                 185

<210> SEQ ID NO 49
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ser Ala Gly Asn His Arg Leu Arg Glu Asp Lys Asp Pro
        35                  40                  45

Arg Lys Met His Ala Thr Ile Tyr Glu Leu Lys Glu Asp Lys Ser Tyr
    50                  55                  60

Asn Val Thr Asn Val Thr Phe Arg Glu Lys Lys Cys His Tyr Ser Ile
65                  70                  75                  80

Gly Thr Phe Val Pro Gly Ser Gln Pro Gly Glu Phe Thr Leu Gly Lys
                85                  90                  95

Ile Lys Ser Asn Pro Gly Met Thr Ser Phe Leu Val Arg Val Val Ser
            100                 105                 110

Thr Asn Tyr Asn Gln His Ala Met Val Phe Phe Lys Lys Val His Gln
        115                 120                 125

Asn Arg Glu Gln Phe Asn Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185

<210> SEQ ID NO 50
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Gly Gln Leu Arg Glu Asp Lys Asp Pro
        35                  40                  45

Trp Lys Met Ser Ala Thr Ile Tyr Glu Leu Lys Glu Asp Lys Ser Tyr
    50                  55                  60

Asn Val Thr Ser Val Arg Phe Arg Leu Lys Lys Cys Ser Tyr Trp Ile
65                  70                  75                  80

```
Tyr Thr Phe Val Pro Gly Ser Gln Pro Gly Glu Phe Thr Leu Gly Gly
                 85                  90                  95

Ile Lys Ser Asn Pro Gly Asp Thr Ser Asn Leu Val Arg Val Val Ser
            100                 105                 110

Thr Asn Tyr Asn Gln His Ala Met Val Phe Phe Lys Tyr Val Ile Gln
            115                 120                 125

Asn Arg Glu Trp Phe Ile Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185

<210> SEQ ID NO 51
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Met Ala Gly Asn Ala Ser Leu Arg Glu Asp Lys Asp Pro
        35                  40                  45

Arg Lys Met Asn Ala Thr Ile Tyr Glu Leu Lys Glu Asp Lys Ser Tyr
50                  55                  60

Asn Val Thr Lys Val Arg Phe Trp His Lys Lys Cys Tyr Tyr Ser Ile
65                  70                  75                  80

Thr Thr Phe Val Pro Gly Ser Gln Pro Gly Glu Phe Thr Leu Gly Asp
                85                  90                  95

Ile Lys Ser Tyr Pro Gly Trp Thr Ser Tyr Leu Val Arg Val Val Ser
            100                 105                 110

Thr Asn Tyr Asn Gln His Ala Met Val Phe Phe Lys Gly Val Arg Gln
            115                 120                 125

Asn Arg Glu Trp Phe Ser Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
                180                 185

<210> SEQ ID NO 52
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 52

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Ile Ala Gly Asn Tyr Ile Leu Arg Glu Asp Lys Asp Pro
            35                  40                  45

Pro Lys Met Arg Ala Thr Ile Tyr Glu Leu Lys Glu Asp Lys Ser Tyr
        50                  55                  60

Asn Val Thr Arg Val Phe Phe Ser Arg Lys Lys Cys Asp Tyr Ile Ile
65                  70                  75                  80

Trp Thr Phe Val Pro Gly Ser Gln Pro Gly Glu Phe Thr Leu Gly Phe
                85                  90                  95

Ile Lys Ser Asn Pro Gly Leu Thr Ser Leu Leu Val Arg Val Val Ser
            100                 105                 110

Thr Asn Tyr Asn Gln His Ala Met Val Phe Phe Lys Trp Val Asp Gln
            115                 120                 125

Asn Arg Glu Val Phe Gly Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Ser Ala Trp Ser His Pro Gln Phe Glu Lys
            180                 185
```